United States Patent
Nakagaki et al.

(10) Patent No.: US 6,657,221 B2
(45) Date of Patent: Dec. 2, 2003

(54) IMAGE CLASSIFICATION METHOD, OBSERVATION METHOD, AND APPARATUS THEREOF WITH DIFFERENT STAGE MOVING VELOCITIES

(75) Inventors: Ryo Nakagaki, Tokyo (JP); Yuji Takagi, Tokyo (JP); Takashi Hiroi, Tokyo (JP); Masahiro Watanabe, Tokyo (JP); Minori Noguchi, Tokyo (JP); Kazuo Aoki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/988,436

(22) Filed: Nov. 20, 2001

(65) Prior Publication Data

US 2002/0171051 A1 Nov. 21, 2002

(30) Foreign Application Priority Data

Apr. 19, 2001 (JP) ........................................ 2001-120467

(51) Int. Cl.$^7$ .............................................. G01N 21/86
(52) U.S. Cl. ................................ 250/559.4; 250/208.1; 250/306; 250/201.3
(58) Field of Search .......................... 250/559.4, 208.1, 250/201.3, 306, 307, 559.45, 559.22; 356/430, 237.1, 238.2, 239.3, 239.7

(56) References Cited

U.S. PATENT DOCUMENTS 6,047,083 A * 4/2000 Mizuno ...................... 382/141

FOREIGN PATENT DOCUMENTS

JP 10-135288 5/1998

* cited by examiner

Primary Examiner—Que T. Le
(74) Attorney, Agent, or Firm—Townsend and Townsend, Crew LLP

(57) ABSTRACT

There are provided an automatic image collection apparatus and method capable of acquiring and automatically classifying fast an image of a defect part caused in a semiconductor wafer production process detected by a defect inspection unit. The image collection apparatus for automatically imaging and collecting images of a plurality of observed parts on a semiconductor wafer is provided with a scheduling portion for deciding the imaging order of the defects and stage moving velocities based on the positional relation of the plurality of observed parts on the wafer and a control portion for feed backing the stage movement amount to the beam deflection amount, thereby imaging and collecting images via an optimal route while moving the stage.

8 Claims, 17 Drawing Sheets

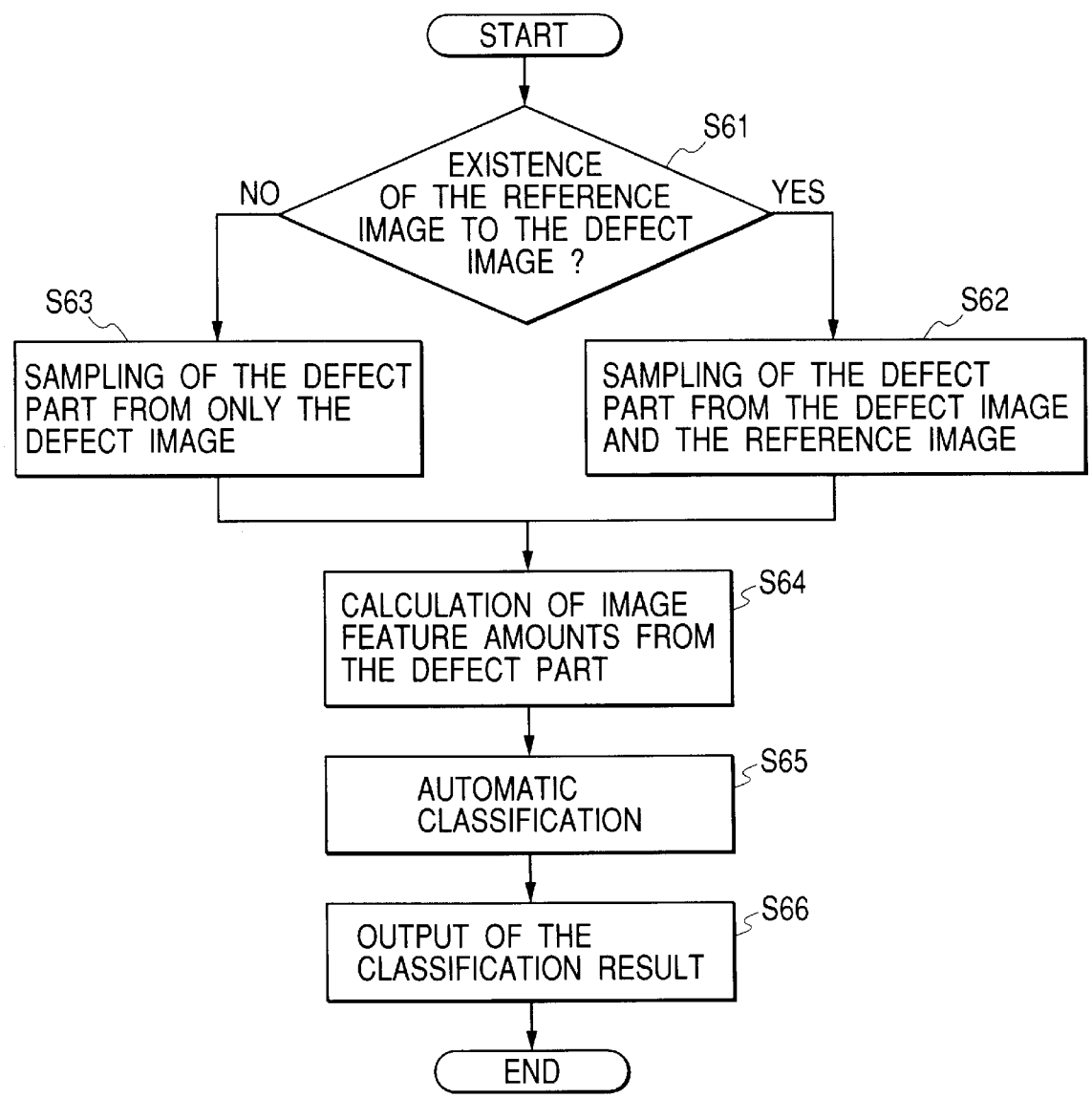

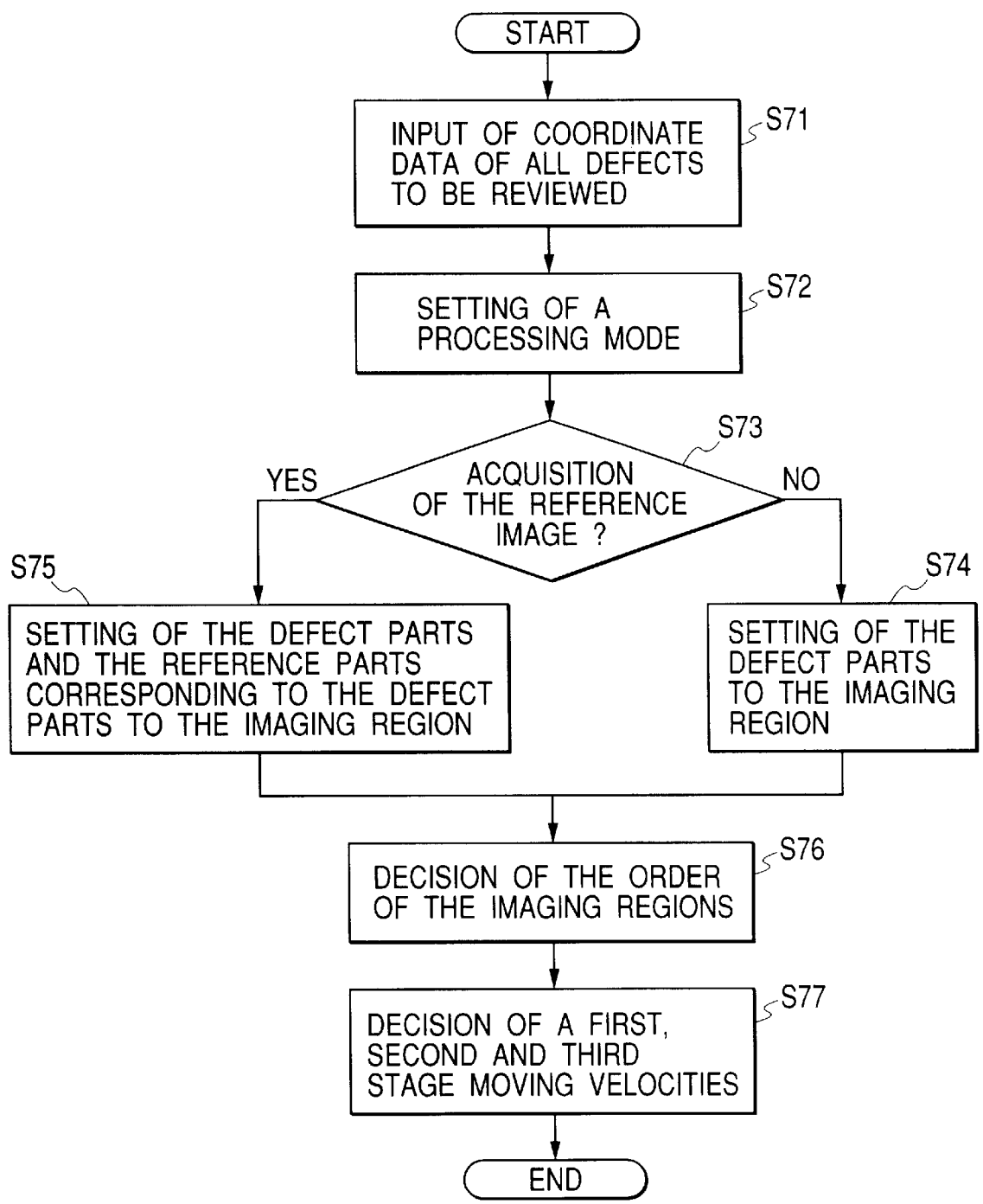

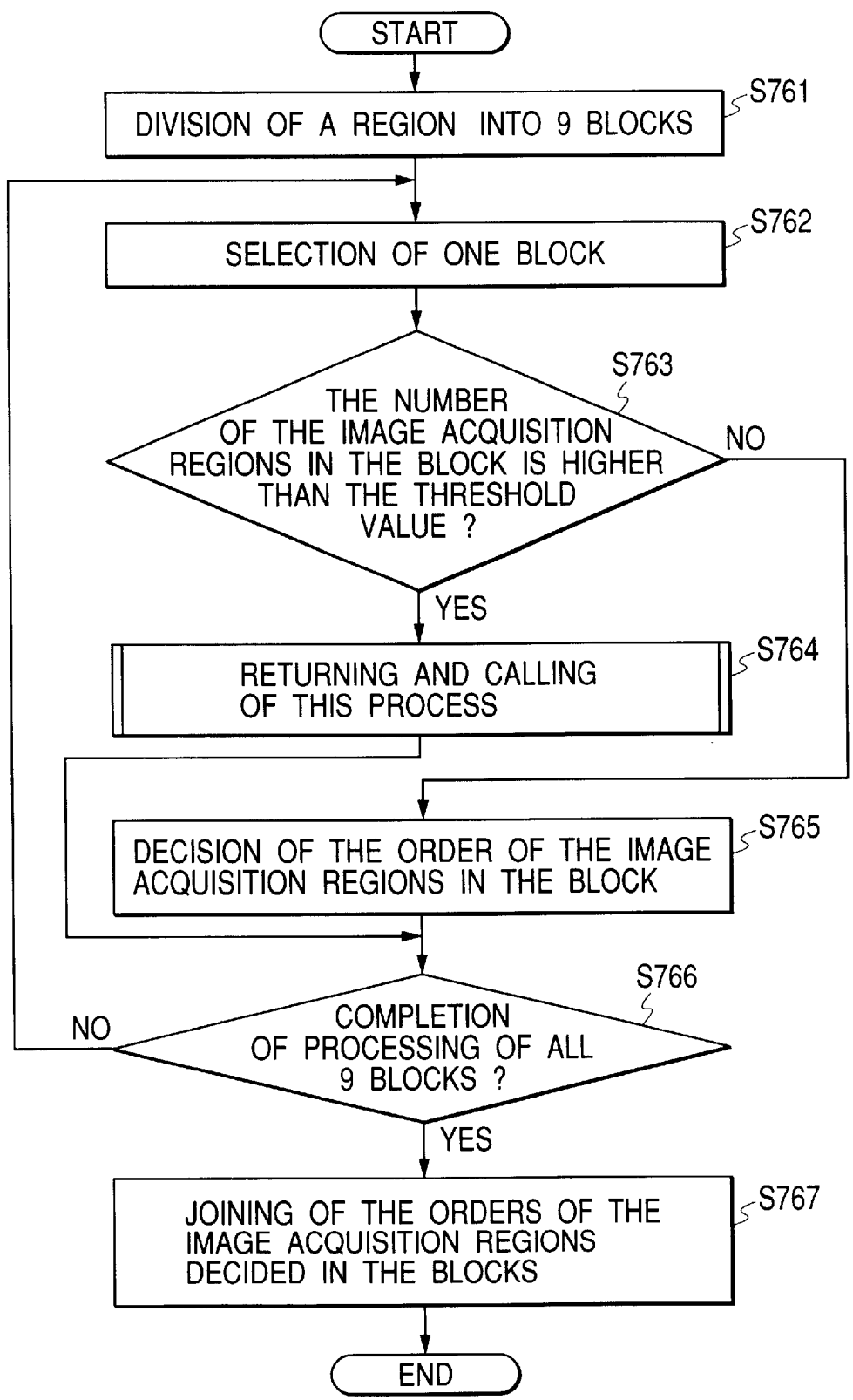

FIG. 9(a)
FIG. 9(b)
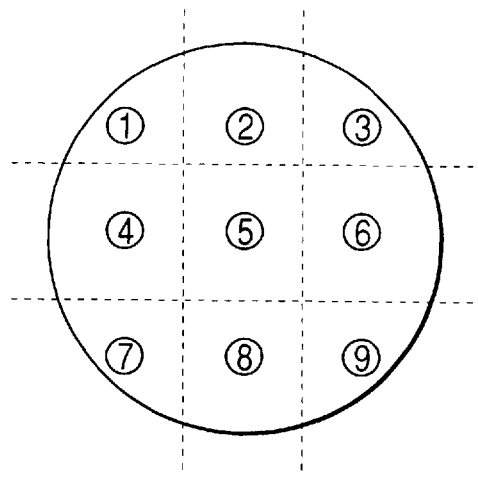
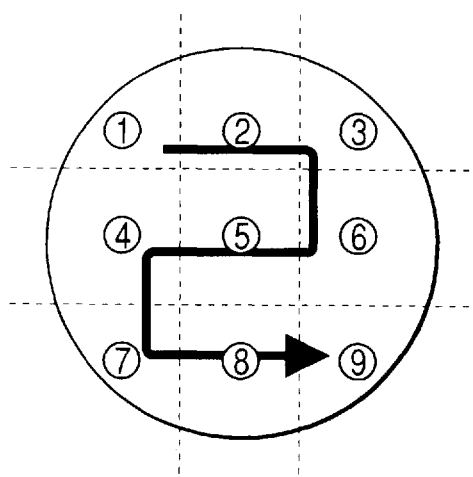
FIG. 9(c)
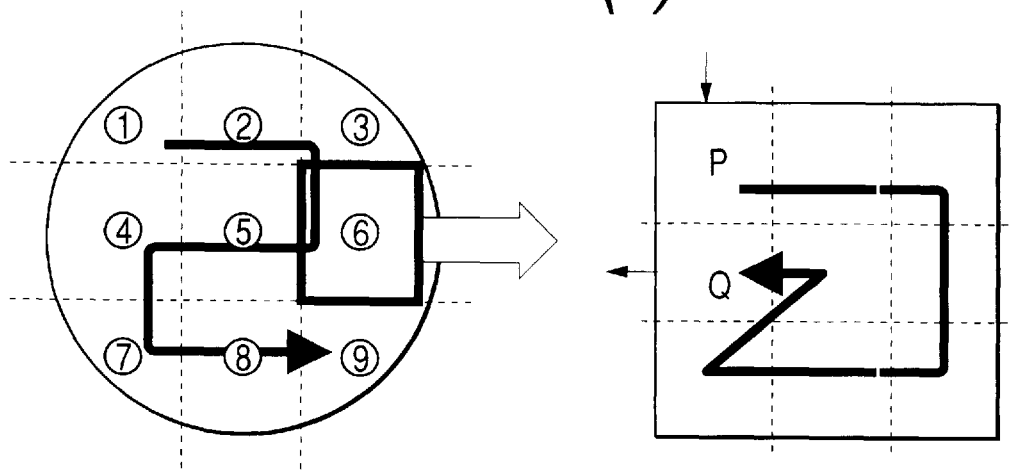
FIG. 9(d)
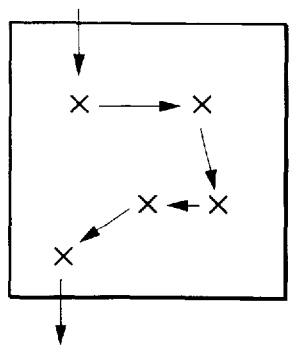
× : IMAGE ACQUISITION REGION TIME : t1

TIME : t2

TIME : t3

TIME : t4

X : DEFECT

IMAGE CLASSIFICATION METHOD, OBSERVATION METHOD, AND APPARATUS THEREOF WITH DIFFERENT STAGE MOVING VELOCITIES

BACKGROUND OF THE INVENTION

The present invention relates to an apparatus and method for automatically observing or classifying defects caused on a semiconductor wafer in a process for producing a semiconductor product.

In a process for producing a semiconductor product, in order to ensure high producing yield, it is necessary to be found various defects caused in the production process and to be taken measures for generation of the various defects, at an early stage. This is typically performed in the following steps.

(1) Detecting the locations of the caused defects or the deposited foreign particles by that a semiconductor wafer to be inspected is inspected by a wafer visual inspection unit or a wafer foreign particle unit.

(2) Classifying the detected defects under each of generating causes by observing (this is called a review) them. This review operation typically uses a review-specific unit having a microscope for observing defect parts at high magnification. Other unit with a review function, e.g., a visual inspection unit may be also used.

(3) Solving measures for each of the causes are taken.

In the case that the number of defects detected by the inspection unit is very high, the review operation needs enormous efforts. Therefore, in recent years, there has been developed actively a review unit having an Automatic Defect Review function for automatically imaging and collecting images of defect parts and an Automatic Defect Classification function for automatically classifying the collected images. Japanese Opened Patent Publication No. Hei 10-135288 discloses a review unit having an Automatic Defect Review function and an Automatic Defect Classification function and using a scanning microscope for an imaging system of it, and a production system.

FIG. 2 shows one example of a prior art ADR processing flow. First, a wafer to be inspected is placed onto the stage of a review unit (S21) and inspection data as results inspected by the inspection unit is read into the review unit from the database (S22). Then, the operator selects and specifies the defect targeted for ADR from the inspection results obtained from the inspection unit (S23). When the throughput of the ADR is high and the defected defect data are small in number, all the defects can be subject to ADR.

The review unit selects one from the specified defects and moves the stage so that the selected defect is positioned in the center of the visual field of an observation system. Thereafter, optimal focus setting is performed and an image of the selected defect is imaged by the observation system (S24). This image is called a defect image. The imaged defect image is stored into a recording medium (e.g., a magnetic disk) in the review unit.

Next, while the stage is moved, an image of the same part of the chip adjacent to the semiconductor chip in which the defect part in the wafer exists, is imaged (S25). This part is formed with the same pattern as that of the defect part. This image is called a reference image to the defect image. The reference image is also stored into the recording medium in the review unit. At the completion of imaging of the reference image, the defect image and the reference image of the next defect are imaged, as described above. These processes are repeated for all the defects to be subject to ADR, and are then terminated (S26).

FIG. 3 shows one example of a prior art ADC processing flow. ADC is a process for automatically deciding a category of the defect by using the defect image and the reference image acquired by ADR. First, the defect part is specified from the defect image and the reference image (S31). Specifically, a differential image is generated by being differentially operated between the defect image and the reference image. As a result, only the part in which the defect image and the reference image are different from each other appears in the differential image, which exhibits the defect part. The feature amounts of the defect are calculated by using the differential image, the defect image and the reference image (S32). The feature amounts quantitatively and numerically express the size of the defect, the shape of the defect, and the contrast on the image of the defect. An Automatic Defect Classification process for deciding the defect category is performed by using the feature amount data (S33).

The prior art ADR and ADC shown in FIGS. 2 and 3 are disclosed in Japanese Opened Patent Publication No. Hei 10-135288. In the prior art, the defect image or the reference image is imaged after the stage is stopped once. The imaging of one imaged part consists of three steps for: (1) moving of the stage to the imaged part, (2) stopping of the stage, and (3) imaging of an image.

When the stage is stopped for imaging, stage control and beam control during imaging can be simplified. On the other hand, the stage must be stopped completely. As the stage has some weight, if a stop command is issued from the control unit of the stage, the stage will not be stopped soon and the time to stop the stage completely is required to some extent. As the stage is moved slightly while the time to stop the stage elapses, if a review image is imaged when the stage is moved slightly, blurring or flow is caused in the image. As the result, the image quality needed for review cannot be obtained. For this reason, it must be waited to start imaging the review image until the time to stop the stage elapses after the command to stop the stage is issued. As this time is longer than the time needed for imaging, the prior art imaging method cannot acquire an image fast.

Here, consider the limit of throughput on the prior art. For simplification, chips produced in a wafer have a 15 mm pitch, and the number of defects per chip is 1. In other words, assume that the interval between defects and the interval between the defect part and the reference part are about 15 mm. The stage moving velocity is assumed to be 50 [mm/sec]. In this case, the time to move a distance of 15 mm is 15/50=0.3 [sec]. Actually, the stage moving needs acceleration or deceleration, and this time must be considered. However, this time is omitted here. The waiting time from stopping of the stage to starting of imaging is 0.2 [sec] as an experience value.

For imaging, a beam needs scanning in two dimensions. If an image of 512×512 pixels as one frame is acquired by scanning at 100 MHz, that is, 10 [n sec/pixel] for one pixel, it need 512×512×10 n[sec]=about 3 [m sec]. As a scanning electron microscope causes much noise in a detected signal, frame addition is typically performed to acquire a high-quality image. The number of the frame additions is assumed to be 16. In the operation of frame addition, a plurality of images of the same part are imaged, so that an average gray-scale value of the same pixel over the plurality of images is obtained as a pixel value of the same pixel, thereby acquiring an image reducing the influence of the noise.

As the number of frames is increased, the image quality is enhanced, but long time is required accordingly. The number of frames is set by considering image quality to be acquired. When 16 frame additions are performed, an electric current value of an irradiation beam is, for example, 200 [pA]. A signal amount n for irradiation to one pixel is n=(200 [pA]×10[nsec]×16)/1.6×10$^{-19}$=200 (one electron is 1.6×10$^{-19}$ [coulomb]. Since a noise of the signal n by statistical fluctuation is $\Delta n=n^{1/2}$, in this case, $\Delta n$=14.1. As an index to quantify the image quality, a standard deviation σ of noise variation to a signal is used to assume that the fluctuation amount $\Delta n$ of the signal is 3σ. From 3σ=14.1, σ=4.7 is determined. With this value, it is found from experience that the image quality needed for review can be ensured.

In imaging, other than the beam scanning, AF (Auto Focus) must be controlled. The time required to analyze various control commands by the internal computer is also needed. These times are different due to the control method or system. Here, the time is 0.5 [sec] as an experience value. As a result, about 3 [msec]×16+0.5=0.55 [sec] is calculated, which is required to image images consisting of 16 frames.

Imaging for one defect needs the steps for: (1) moving to the defect part (moving the stage by 15 mm), (2) waiting for stage stopping, (3) imaging, (4) moving to the reference part (15 mm), (5) waiting for stage stopping, and (6) imaging. The time needed for this is calculated using the above-mentioned value to determine about 0.15+0.2+0.55+0.15+0.2+0.55=1.8 [sec]. It is converted to the number of defects imaged per hour, a throughput is 3600 [sec]/1.8=2000 DPH (Defect Per Hour). An upper limit of the throughput of the prior art ADR can be considered about 2000 DPH. The throughput of a review unit using a scanning electron microscope currently on the market is several hundred DPH. With the influence of various overheads caused in each of the units, it is found that the throughput lower than the upper limit test-calculated above can be only realized.

Making semiconductor products finer is advanced increasingly. The number of defects detected from one wafer is enormous. It is sufficiently possible that about 10000 defects can be detected from one wafer. The throughput of the visual inspection unit or the foreign particle inspection unit for detecting these defects is increased. By way of example, the throughput of a foreign particle inspection unit using a laser scattering light detection method is about 100 [sec] per wafer. The throughput of the foreign particle inspection unit is thus high. The foreign particle inspection unit is often used in the production process as a tool for inspecting the same wafer to examine the transition of the number of defects.

To grasp what defect is caused in a wafer, all the defects on the wafer must be reviewed (100% review). In the prior art, the 100% review requires above five hours per wafer. In the production process, the time for inspection and review does not contribute directly to production. It is not preferable that one wafer is reviewed for above five hours. For this reason, several to several hundred defects are sampled from all the defects. Only the sampled defects have been reviewed.

In sampling, when the defect type is unbalanced, the defect causing state cannot be grasped suitably. As the result, it can be impossible to make full use of the inspection result data.

Therefore, there will be required in the future a unit capable of reviewing the defect data of all the defects data (about 10000) on one wafer for about one hour.

In the prior art, when images of a plurality of defect parts detected by the defect inspection unit are imaged automatically, imaging is performed after the stage is positioned for each of the defects so that the defect part comes into the center of the visual field of the imaging system such as a microscope. In other words, imaging is performed after the stage is stopped once for each of the defects in the position in which the defect comes into the center of the visual field.

Since the stage has some weight, several seconds is typically needed from issuing of a stop command from the stage control system to actual stopping of the stage. During the several seconds, the stage is moved slightly. When imaging is performed in this state, blurring or flow is caused in the image. An image capable of corresponding to the review cannot be acquired. When the stage is stopped for imaging, the imaging must be waited while the stage is stopped completely.

In the prior art, the stage is moved or stopped for each of the imaged parts. The throughput of the imaging cannot be increased.

SUMMARY OF THE INVENTION

The present invention solves the foregoing problems of the prior art, and an object of the present invention is to provide an image collection apparatus capable of collecting images of the observed parts with high throughput.

Accordingly, in the present invention, a scanning electron microscope is used as an imaging system to control the irradiation position of an electron beam based on the positional information of a stage and the positional information of an imaged part, whereby imaging is possible while moving the stage.

According to the present invention, in a method for moving a stage with a sample placed thereon based on the positional information of a plurality of locations to be observed on the sample so as to sequentially place the plurality of locations to be observed into an observation visual field which are observed sequentially, the location to be observed placed into the observation visual field is imaged while moving the stage to acquire an image of the location to be observed, the acquired image is classified, and the classified image is stored.

According to the present invention, in a method for moving a stage with a sample placed thereon to sequentially image a plurality of locations on the sample, and classifying images acquired by the imaging, the stage is moved based on the positional information of the plurality of locations to be imaged on the sample to sequentially place the plurality of locations to be imaged into an imaging visual field, the location to be imaged placed into the imaging visual field is imaged while moving the stage, and then, 10000 images can be acquired for one hour, whereby the acquired image is classified to be stored.

According to the present invention, in a method for moving a stage with a sample placed thereon to sequentially image a plurality of locations on the sample, and classifying images acquired by the imaging, the stage is moved at a first velocity based on the positional information of a plurality of locations to be imaged on the sample to sequentially place the plurality of locations to be imaged into an imaging visual field, the location to be imaged placed into the imaging visual field is imaged while moving the stage at a second velocity lower than the first velocity to acquire an image of the location to be imaged, the acquired image is stored.

According to the present invention, in a method for sequentially imaging a plurality of locations on a sample to classify the images acquired by the imaging, the stage with a sample placed there on is moved based on the positional information of the plurality of locations to be imaged on the sample to sequentially place the plurality of locations to be imaged into an imaging visual field, and the location to be imaged placed into the imaging visual field is imaged while moving the stage, whereby images of the plurality of locations to be imaged on the sample are acquired without stopping movement of the stage, and the acquired images are classified.

According to the present invention, in a method for observing a sample at a first magnification to detect a plurality of defects, storing the positional information of the plurality of defects detected, and observing the sample at s second magnification higher than the first magnification based on the positional information of the plurality of defects stored, whereby when the plurality of defects are observed at the second magnification, the plurality of defects can be observed without stopping movement of the sample.

According to the present invention, in a method for sequentially imaging a plurality of locations on a sample to acquire an image, the order of moving the sample is set so that the plurality of locations are sequentially placed into in an imaging visual field, the sample is moved to the imaging visual field in accordance with the set order, and the location placed into the imaging visual field of the plurality of locations is imaged while moving the sample to acquire an image.

These and other objects, features and advantages of the invention will be apparent from the following more particular description of preferred embodiments of the invention, as illustrated in the accompanying drawings.

BRIEF DESCRIPTION OF THE DRAWINGS

FIG. 6 is a diagram showing the sequence of an image automatic classification process according to the present invention;

FIG. 7 is a diagram showing the sequence of imaging scheduling according to the present invention;

FIG. 8 is a diagram showing the sequence for finding a shortest moving path between defects according to the present invention;

FIG. 9 is a diagram of assistance in explaining the process for finding a shortest moving path between defects according to the present invention;

DESCRIPTION OF THE PREFERRED EMBODIMENTS

Embodiments of the present invention will be described hereinbelow.

Figure 1:
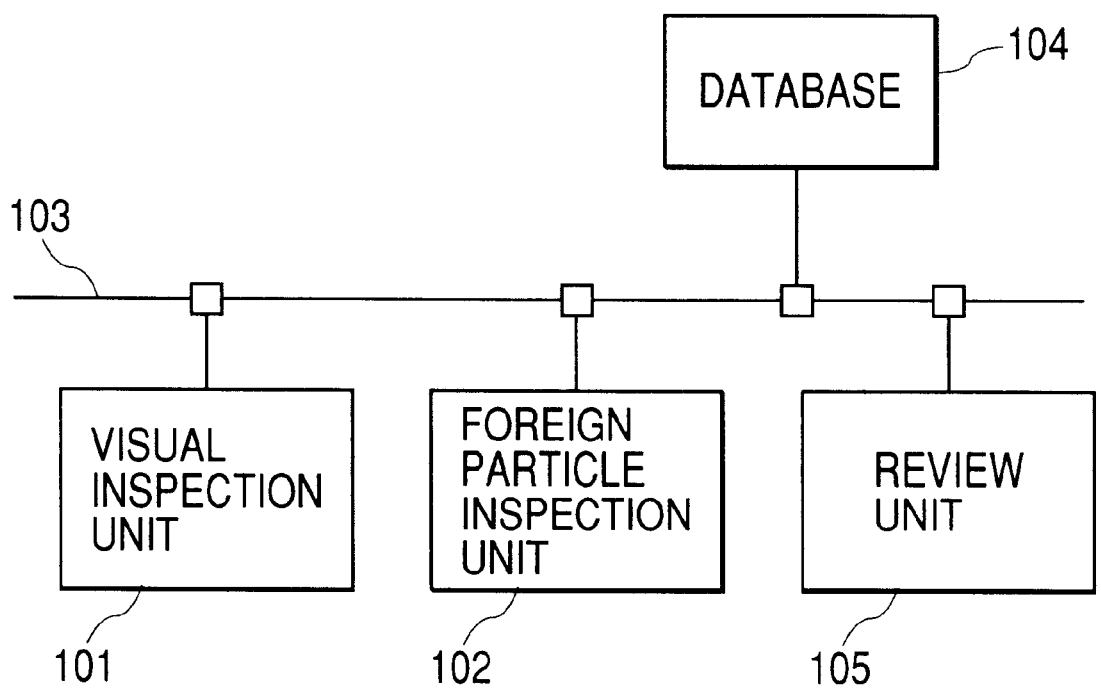
FIG. 1 is a block diagram showing the construction of a defect inspection system of a semiconductor.
Figure 2:
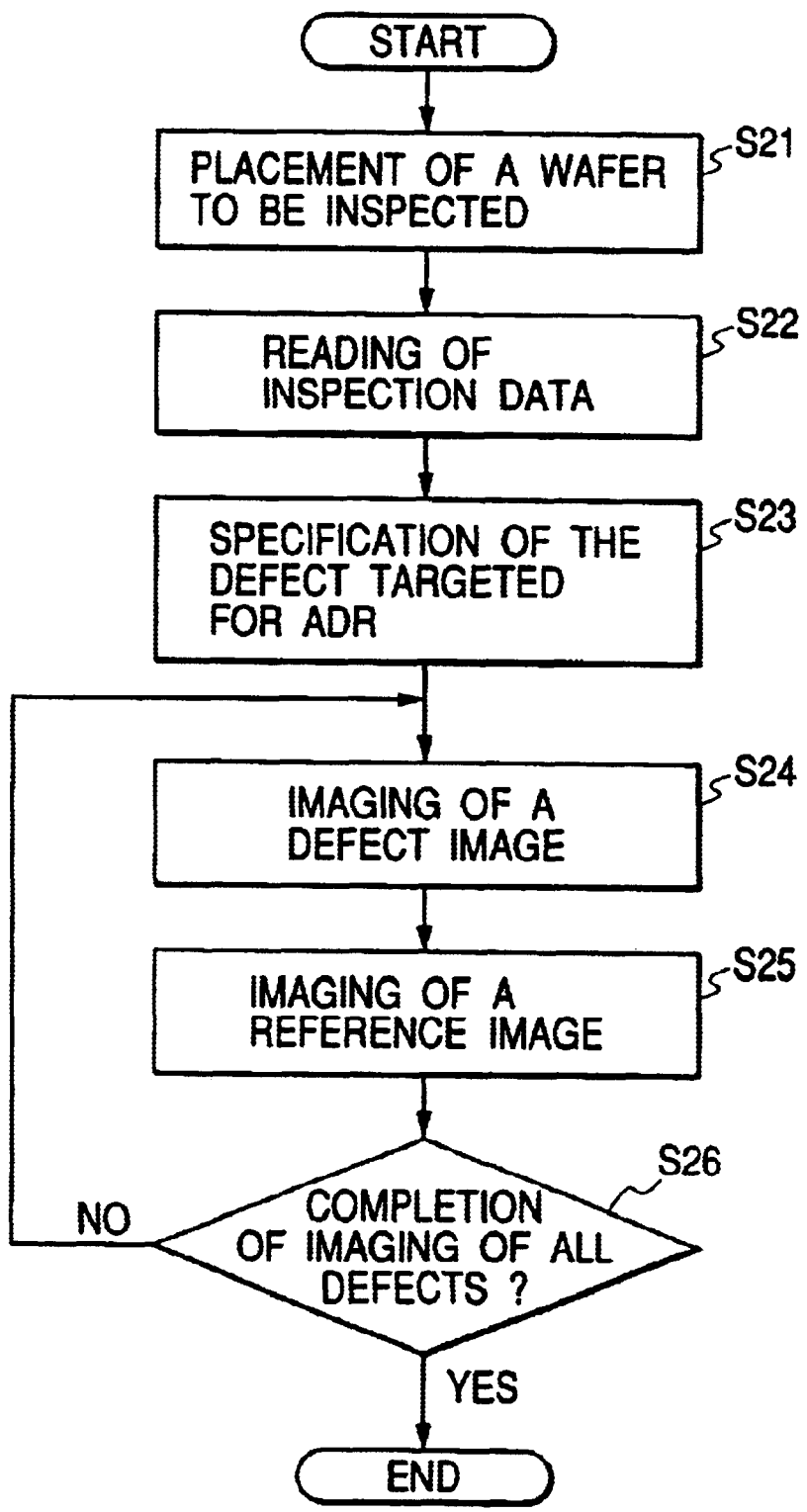
FIG. 2 is a diagram showing a prior art ADR processing flow.
Figure 3:
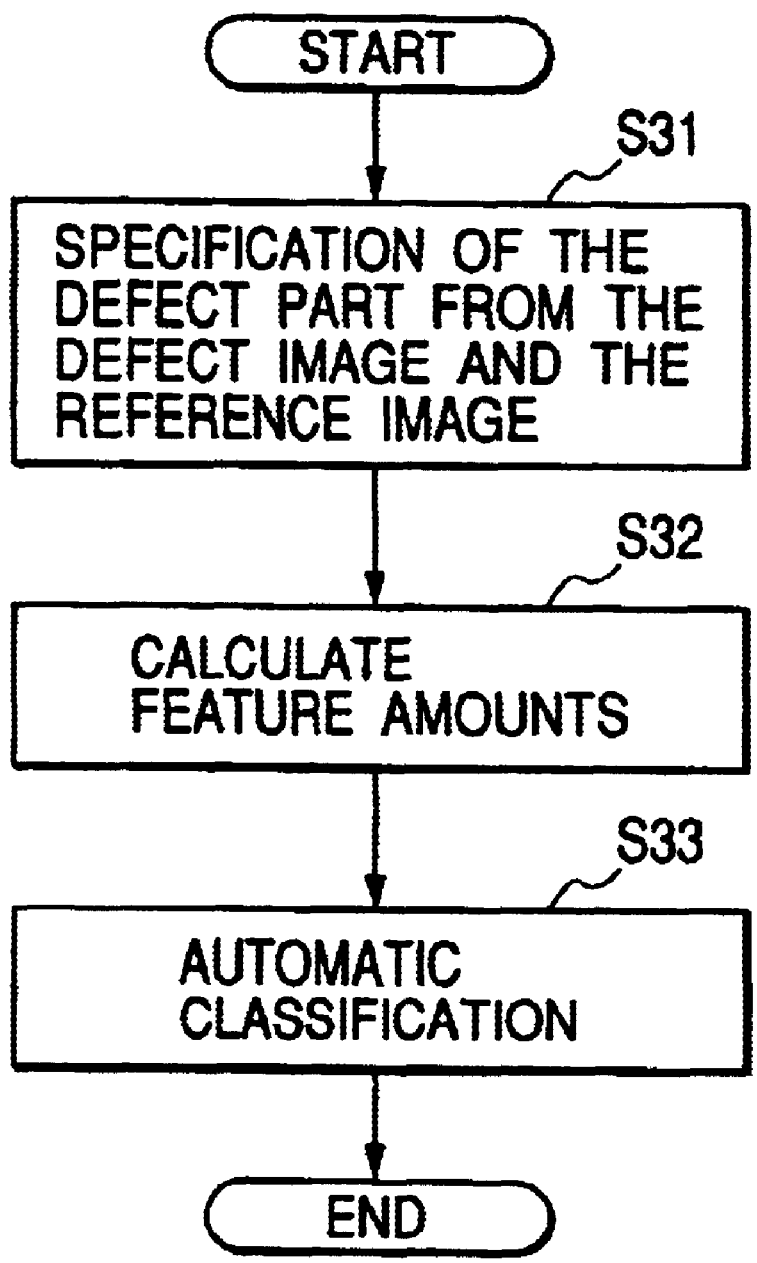
FIG. 3 is a diagram showing a prior art ADC processing flow.

FIG. 1 shows the construction of a defect inspection system of a semiconductor. A semiconductor wafer is inspected using a visual inspection unit (system) 101 and a foreign particle inspection unit (system) 102 in order to detect defects caused and foreign particles deposited in the production process. In the description described below, these units for inspecting defects (the visual inspection unit (system) 101 and the foreign particle inspection unit (system) 102) will be generally called as an inspection unit.

The inspection unit detects defects of a pattern formed on the surface of a wafer, for example, a break (open) in the pattern, a short circuit between the pattern and the adjacent pattern, and foreign particles deposited on the surface of a wafer. The inspection unit then outputs, as an inspection result, the coordinate position of each of the defects on the wafer together with identification data, processing data, and lot data of the wafer. The inspection result outputted is stored from the inspection unit into a database 104 through a recording medium such as a floppy disk or a network 103. The database 104 holds data of various product types produced and inspection data inspected on each of the production processes, so as to fetch, as needed, inspection result data by each of products, by each of processes, and by each of production lots.

To examine the contents of the defect detected, the observation operation of the defect (review operation) is performed. A review unit (system) 105 is typically equipped with an optical electronic microscope or an electronic microscope of an electron beam type for observing micro defects. The review unit has a stage for placing a wafer thereon, and a function in which when the operator selects and specifies the defect to be observed from the inspection results, the stage is moved automatically so that the defect is placed into the observation visual field of the microscope. For review, a visual inspection unit having the above-mentioned review function may be also used, in place of such a review-specific unit.

The semiconductor wafer in which the inspection by the visual inspection unit is completed is set to the review unit (system) 105. The inspection result is read through the network 103 into the database 104. In the case of manual review, the operator typically specifies the defect to be observed from input means such as a keyboard or a mouse so as to observe the defect by the microscope. The operator visually judges the attribute (category) of the defect to input the code from the input means.

The category code set in each of the defects in the review unit 105 is stored through the network 103 into the database 104. Using the category code, the defect causing state such as the number of defects for each of the categories viewed by each of products, by each of processes, and by each of periods can be grasped to obtain data necessary for taking measures so as to eliminate the cause being generated the defect. In the case that the above-mentioned review operation is performed manually, these operations need lots of time and efforts. The review operation is not performed to all the defects detected by the inspection unit, but is typically performed to only some of the observed defects reduced from the defects by some method.

There has been recently developed a review unit having the above-mentioned Automatic Defect Review (hereinafter, ADR) function for continuously and automatically performing instruction of the observed defects, moving of a stage, and acquisition of an image of a defect part. There has been also developed a review unit having an Automatic Defect Classification (hereinafter, ADC) function for using image data of a defect part by the automatic review to automatically judge and output the defect category.

In the following description, as an imaging unit for review, there will be considered a review unit using a scanning electron microscope, SEM (Scanning Electron Microscopy) capable of imaging defects at a high resolution of several nm (nanometers).

Figure 4:
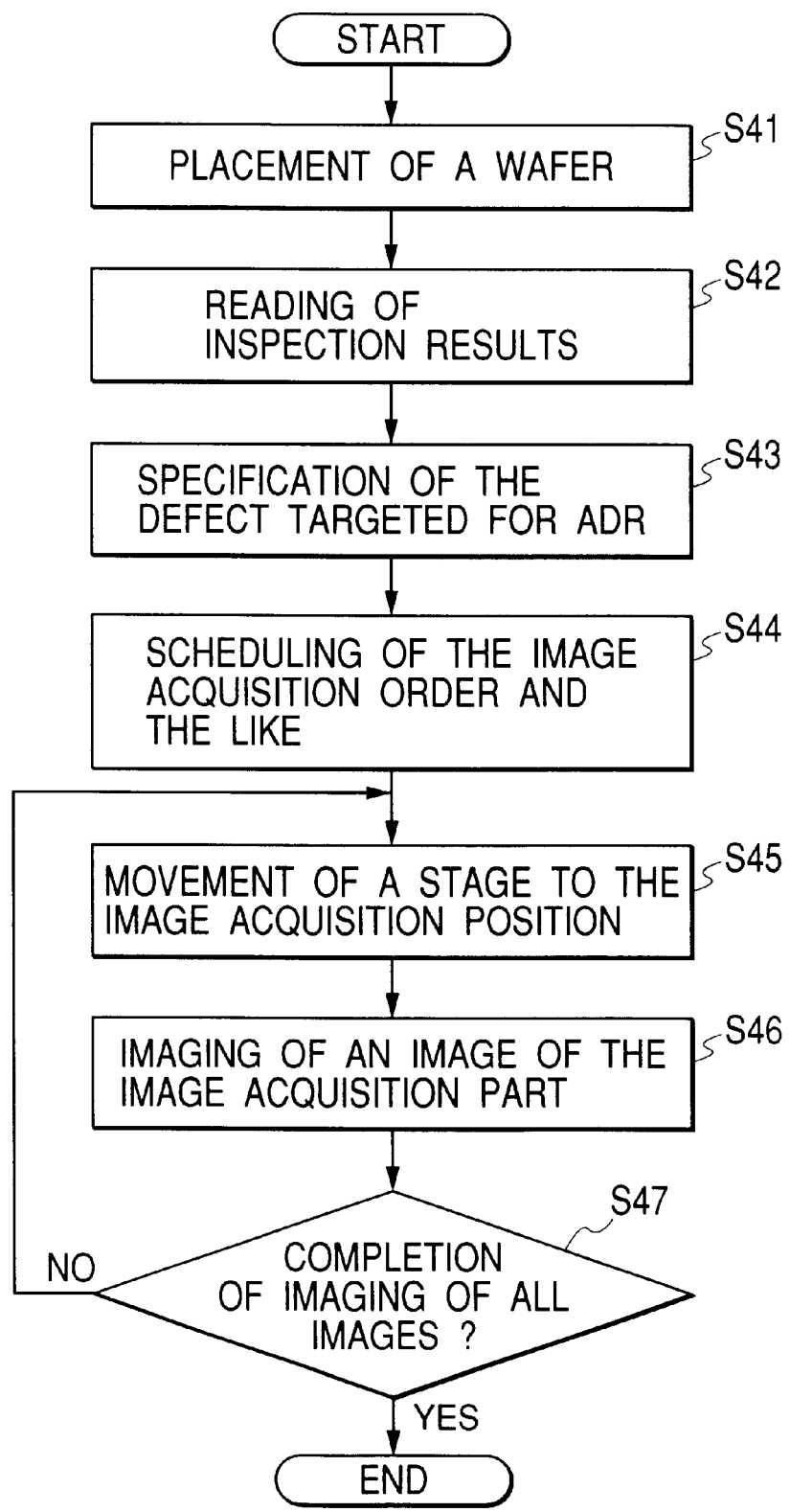
FIG. 4 is a diagram showing the sequence of the ADR of an image collection apparatus according to the present invention.
Figure 5A:
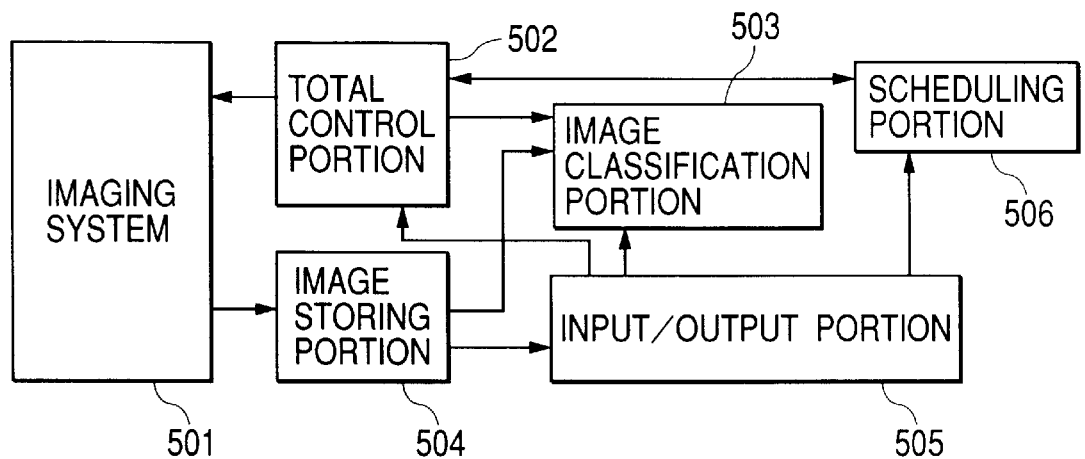
FIG. 5(*a*) is a block diagram showing the construction of the image collection apparatus according to the present invention, and FIG. 5(*b*) is diagram showing the schematic construction of an imaging part.
Figure 5B:
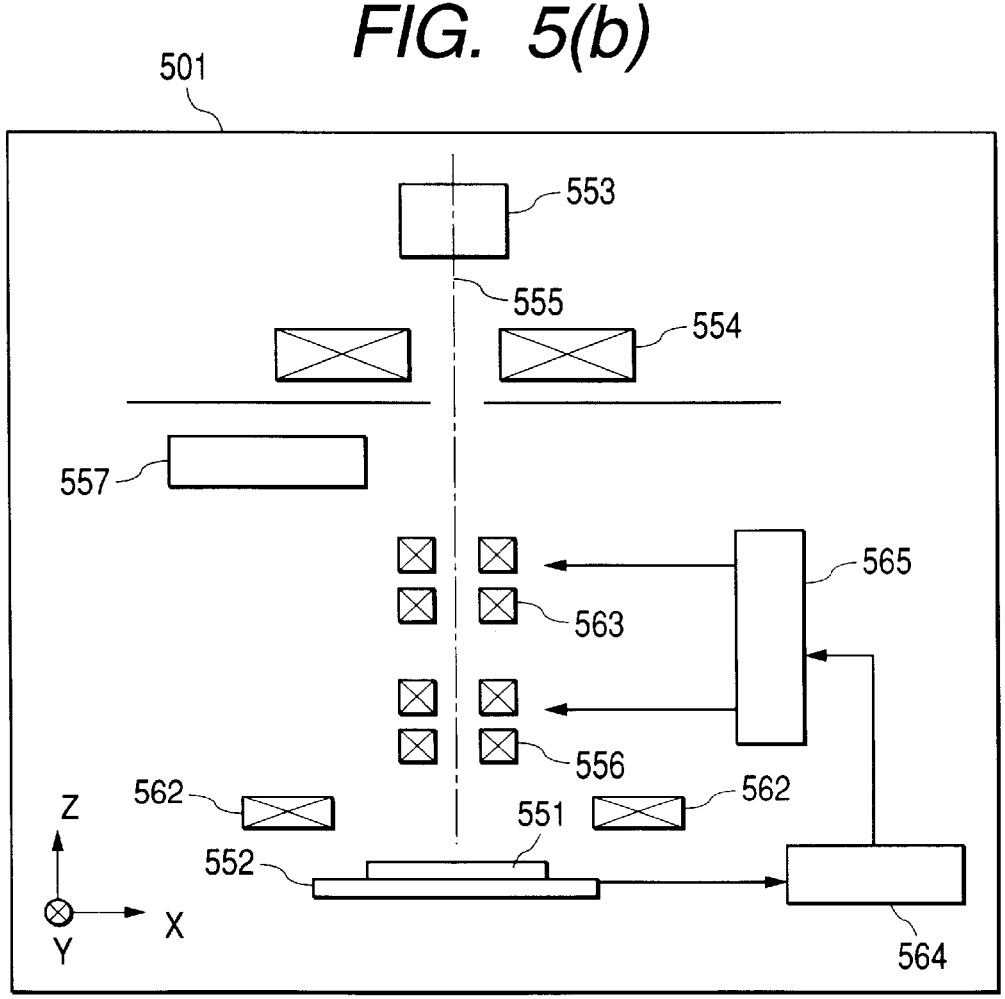

FIG. 4 shows the sequence of a process of an image collection apparatus according to the present invention. FIG. 5(a) shows the entire construction of the image collection apparatus according to the present invention, and FIG. 5(b) shows the construction of an imaging part. This apparatus has an imaging portion 501, a total control portion 502, an image storing portion 503, an image classification portion 504, an input/output portion 505, and a scheduling portion 506. An object wafer 551 is placed onto a stage 552 (S41). The inspection result of the wafer is read through the network 103 into the total control portion 502 (S42).

The operator specifies the given number of the defects targeted for ADR through the input/output portion 505 from the defects of the inspection result (S43). The specified contents are stored into the total control portion 502. Based on the positional information of the specified defect, the scheduling part 506 schedules the order of the defects to be subject to ADR, the stage moving velocity when imaging the defects, and the stage moving velocity between the respective parts (S44). The scheduling result is stored into the total control portion 502. When the input/output portion 505 instructs to start ADR, the total control portion 502 controls the respective parts, not shown, of the stage control portion, the beam control portion, and the objective lens control portion in the imaging system 501 to perform ADR as scheduled.

The procedure for imaging is as follows. The stage is moved at a first moving velocity previously scheduled so that the part to be imaged is placed to the border of the imaging visual field (S45). Here, the visual field is a region onto which a beam can be scanned by first deflector 563. When a plurality of imaged parts are adjacent to each other and the visual field is larger than the distance of adjacent imaged parts, one visual field may include a plurality of imaged parts.

The part to be imaged is specified by the position of a chip and the coordinate value in the chip on each of the imaged parts given by the inspection unit. Since the coordinate value is a value measured by a system different from the coordinate system of SEM, it does not always correspond to the coordinate value of the coordinate system of the SEM. In this case, before ADR, it is necessary to calibrate the coordinate of each of the defects to delete shifting of the coordinate of the inspection unit and the SEM.

After that, the stage is moved at a second moving velocity scheduled. Imaging is performed while moving the stage (S46). The imaged part continuing to move in the visual field in synchronization with the stage movement is irradiated with an electron beam for imaging. When imaging of all the imaged parts included in the visual field is completed, the stage is moved at a third moving velocity scheduled to the position in which the next imaged part is placed into the visual field. The sequence is repeated until imaging of all the defects to be subject to ADR is completed (S47). With FIGS. 10 and 11, there will be described later methods for deciding the imaging order, a first stage moving velocity (a stage moving velocity to bring the imaged part into the visual field), a second stage moving velocity (a stage moving velocity during imaging), and a third stage velocity speed (a stage moving velocity to bring the next imaged part into the visual field after the imaged part is imaged).

With FIG. 5(b), the imaging method of the review unit according to the present invention will be described in greater detail. A focusing lens 554 focuses an electron beam 555 irradiated by an electron gun 553. A track thereof is scanned by the first deflector 563 and second deflector 556 in the X and Y directions in the drawing, and is then focused by objective lenses 562, and is irradiated onto the sample wafer 551. A secondary electron is caused from the sample surface irradiated with the electron beam. The track of the secondary electron emitted in the z direction in the drawing is bent in the direction of a detector 557 by the influence of the magnetic field and the electric field, not shown, and is then detected by the detector 557. The intensity of the detected secondary electron is converted to an electric signal for amplification. Thereafter, the amplified signal is converted to a gray-scale image signal having an intensity exhibiting brightness, and is then displayed on the input/output portion 505 or is converted to digital data to be stored into the image-storing portion 504.

Figure 17:
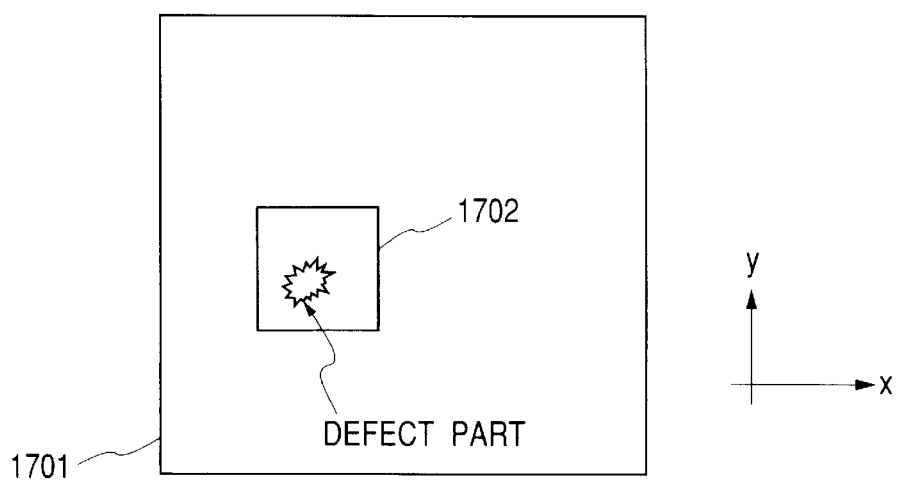
FIG. 17 is a diagram of assistance in explaining an imaging visual field and an imaged part according to the present invention.

FIG. 17 is a schematic diagram of the part to be imaged viewed from top. The numeral 1701 in the drawing denotes an imaging visual field. This region can deflect an electron beam by the first deflector 563. The numeral 1702 in the drawing denotes an imaging region. The first deflector 563 positions an electron beam to the upper left of the region 1702, which is then scanned with the electron beam by the second deflector 556 and the first deflector 563 in two dimensions to acquire image data of the imaging region 1702.

The imaging region 1702 must be of a size so that the defect part can be of a suitable size in a digital image, and is typically several micrometers square. The imaging visual field 1701 is, for example, several hundred micrometers so as to be sufficiently large to the imaging region 1702.

Figure 18A:
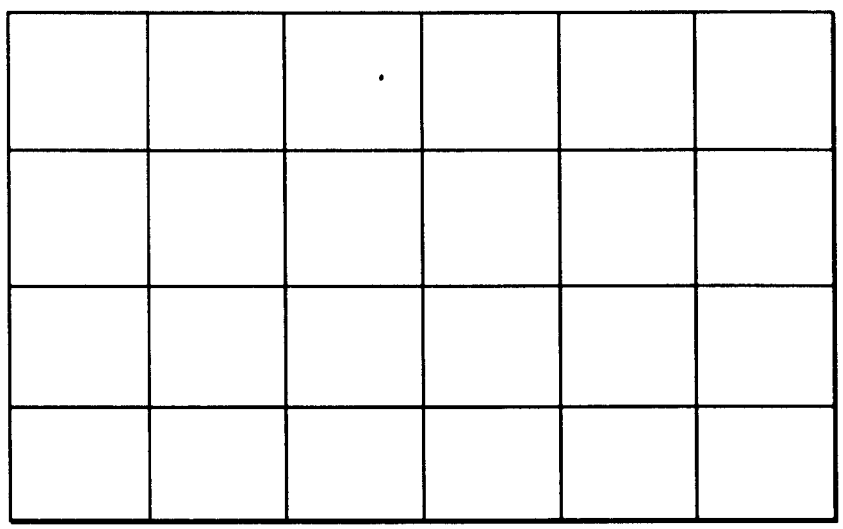
FIG. 18 is a diagram of assistance in explaining imaging deflection according to the present invention.
Figure 18B:
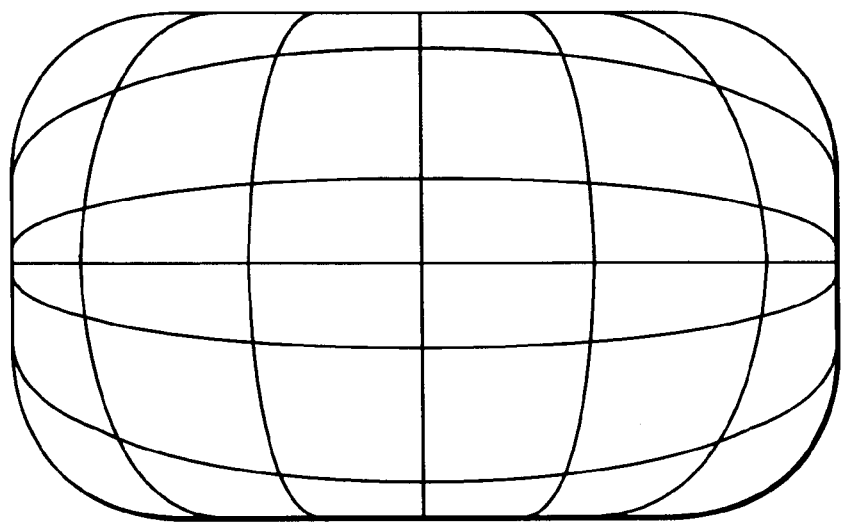

When an image is detected using an electron beam as in the present invention, the imaging visual field 1701 is large to distort the image. This is solved by correction processing an image distortion described below. First, a regular pattern as shown in FIG. 18(a) is imaged with a large visual field and is stored as imaging data. FIG. 18(b) is an image imaged and shows a state that the pattern is distorted. Here, assume that FIG. 18(b) is obtained from FIG. 18(a) by a certain geometric conversion. To obtain FIG. 18(a) from FIG. 18(b), the above-mentioned reverse conversion may be performed. The reverse conversion equation is assumed to be an equation for correcting FIG. 18(b) to calculate and store a correction equation on each of the pixels of FIG. 18(b) in order to create FIG. 18(a) from FIG. 18(b). When the image is imaged, it is possible to correct the distortion image by using the above-mentioned correction equation. As the degree of the image distortion is inherent to each of the units, each of the units previously acquires image data for correction and calculates the correction equation in accordance with the image data and stores the correction equation. Thereafter, on each of the units, it is possible to correct the distortion image by simply using the correction equation being inherent. As the result, the time to acquire an image will not be affected.

Figure 19:
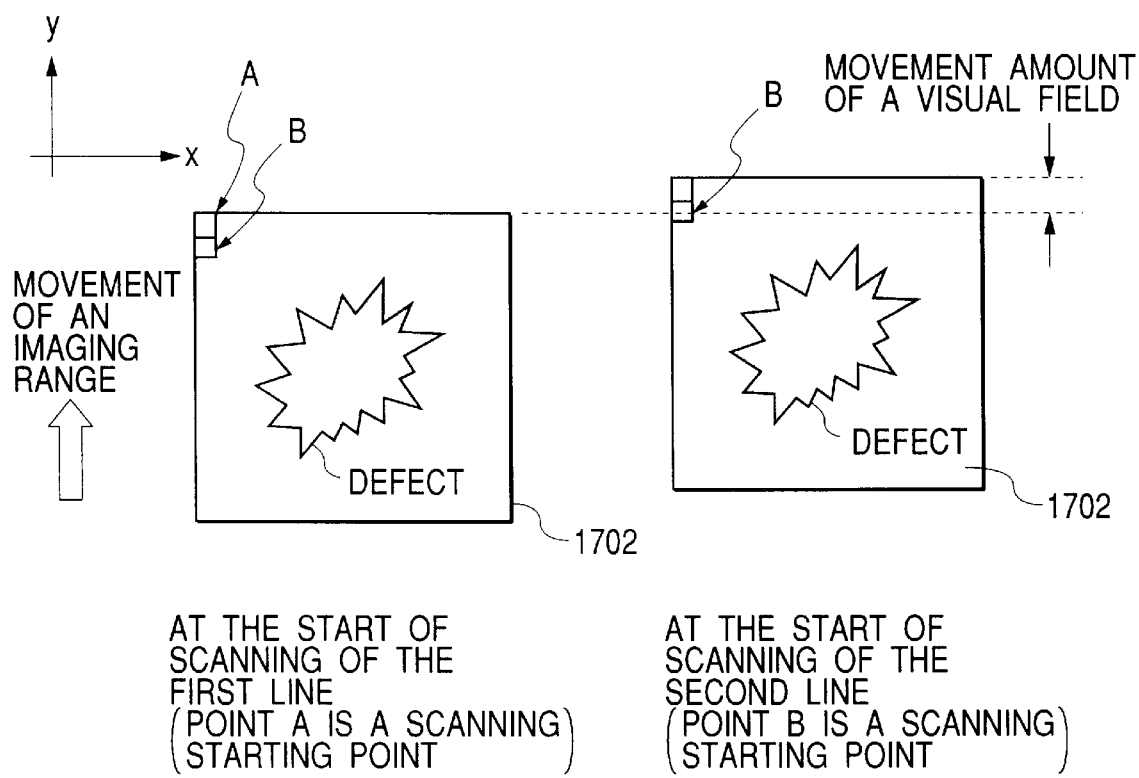
FIG. 19 is a diagram of assistance in explaining an imaging method according to the present invention.

In the present invention, a method for imaging image data while moving the stage will be described hereinbelow. A stage-measuring device (laser measuring device) 564 in FIG. 5 has a function for measuring the position of the stage to transmit the contents to a deflection control portion 565. FIG. 19 schematically shows the state of imaging. When the stage is moved in the y direction, the visual field is moved in the direction opposite to the stage. In this case, when the visual field is fixed, the imaged part 1702 is moved in the visual field in the y direction.

First, the first and second deflectors are used to position the irradiation position of the electron beam to point A to irradiate the beam. Then, the electron beam scans the irradiation position in the x direction to scan the next row. Since the stage continues to move in the y direction while the electron beam scans in the x direction, the irradiation range of the beam is moved in the y direction. A movement amount in the y direction of the imaged part being scanning in the x direction is measured by the stage-measuring device 564 to give the value to the deflection control portion 565. The deflection control portion 565 controls the deflection amount of the second deflector 556 in the y direction so that the beam is irradiated linearly onto the sample in parallel with in the x direction.

When one scanning in the x direction is completed, the next row is scanned in, the x direction. In this case, the stage position at this time is measured by the stage-measuring device 564 to give the value to the deflection control portion 565. At the start of scanning of the next row, the deflection control portion 565 controls the second deflector 556 so as to irradiate the beam to the scanning starting point B. From the point B, the beam is scanned in the x direction to obtain image data. Hereinafter, image data is obtained in the same manner. Thus, the movement amount of the stage is monitored to feed back to the beam position, whereby an image is acquired while moving the stage.

An image acquisition method for performing an addition process to prevent the influence of noise will be described hereinbelow. As described above, the prior art review unit using a scanning electron microscope performs frame addition to prevent the influence of noise. Also in the present invention, addition can reduce the influence of noise. In order to do that, two ways of frame addition and line addition can be realized. In the frame addition, a plurality of image data are acquired for each frame to create an addition image from the plurality of images acquired.

The step is performed as follows. First, the first frame is imaged while moving the stage. Then, at the completion of imaging of the first frame, a movement amount of the beam irradiation starting position of the frame is determined from the stage movement amount obtained from the stage-measuring device 564. Using the result, the deflection control portion 565 controls the first or second deflector so that the beam irradiation starting position of the second frame is the same as the beam irradiation starting position of the first frame. Thereafter, an image of the second frame is acquired. This process is performed to the predetermined number of frames to process a plurality of images acquired, thereby creating an image reducing the influence of noise.

On the other hand, in the line addition, after one line is scanned (in the x direction), the deflection control portion 565 controls the next scanning starting position to be the same as the first scanning position. The same line is continuously scanned the predetermined number of times to obtain image data, and then, image data of the next line is obtained.

As described above, according to the present invention, as the beam irradiation position is controlled with the result of the position measurement of the moving stage being used, an image can be acquired while moving the stage. While the stage is accelerated or decelerated, it can be predicted how far the next position to irradiate the beam is moved from the stage position measured by the stage-measuring device (laser measuring device), and then, the beam can be irradiated based on the prediction result. According to this method, imaging can be performed in the case that velocity irregularities are caused when the stage is moved with constant velocity, and in the interval of that velocity of the stage is reduced by the time the stage is stopped completely on the case that the stage is stopped as the prior art. A range to be met by the stage moving velocity when an image is acquired while moving the stage will be described later with FIGS. 10 and 11.

FIG. 6 shows the sequence of the Automatic Defect Classification process (ADC process) performed by the image classification portion 503. The ADC process may be performed in synchronization with or not in synchronization with the imaging process by ADR. When a pair of the defect image and the reference image can be used to each of defect parts (S61), the differential image process specifies the defect part of the images (S62). Thereafter, the image process calculates the image feature amounts such as the brightness (gray-scale), shape or the like on the specified defect part (S64). These values are checked against the previously set database to perform automatic classification (S65). On the other hand, when the reference image of each of the defect parts is not acquired in S61, the defect part is sampled from only the defect image (S63). The image feature of the defect part is calculated based on the sampling result (S64) to perform automatic classification (S65). For example, when the defect image includes a period pattern such as a memory cell or the like, the defect part can be sampled as a defect region from only the defect image by judging that a region not having the periodicity in the image is the defect region.

FIG. 7 shows the flow of a scheduling process performed by the scheduling portion 506. First, the coordinate data of all the defects to be reviewed are inputted (S71). Then, the input/output portion 505 sets the processing mode of the scheduling (S72). The processing mode is a flag value about whether the reference image of each of the defects is acquired or not. When the reference image is not acquired in S73, only the defect part is the imaging region as image (S74). When the reference image is acquired in S73, the reference part of each of the defect parts in addition to the defect part is the imaging region as image (S75). The reference part typically refers to the same part of the adjacent chip in the same position in the chip as the defect image. However, the reference part is not limited thereto, and may be any part on the wafer, which is formed with the same circuit pattern as that of the defect part. Scheduling is performed next.

The first step of scheduling is to decide the order of the image regions to be reviewed (S76). This determines a relative distance between the imaging parts as image from the coordinate values thereof, thereby finding a path in which the distance of the stage movement necessary for imaging all the imaging regions is shortest. When the number of the defects on the wafer is high, the calculation time to find the shortest path in the strict meaning can be too long. In such a case, a quasi-optimal path is found.

FIG. 8 is a diagram showing the processing flow of one example of a process to find a shortest path. FIG. 9 is a diagram of assistance in explaining the process. First, a semiconductor wafer is divided into a plurality of blocks (S761). FIG. 9(a) shows an example in which the block is divided into nine. Then, the order of the divided nine blocks is defined. The order is defined so that the moving distance from the block to the block is shortest.

The starting and ending blocks are first fixed to be ①, ⑨, respectively. The processing flow is then started from ① to pass once, without fail, from ① to ①, thereby finding a shortest path of the paths to reach ①. The result is shown in FIG. 9(b). When the number of nodes is low in this way, the length of the path is calculated in a round-robin manner to select the shortest path. Other than a solution shown in FIG. 9(b), solutions of the shortest path exist. In such a case, any one of the solutions is optionally selected as the solution.

Each of the blocks of FIG. 9(a) are further divided into 9 small blocks, and then, the order of the small blocks is defined, as in the case of determination of FIG. 9(b). The starting point and the ending point for defining the order of the small blocks use the positions across the boundary of each of the blocks when the order of each of the large blocks is traced. For example, in FIG. 9(c), the starting small block is No. P, and the ending small block is No. Q. FIG. 9(c) shows a state that the block ⑥ in FIG. 9(a) is further blocked to decide the order.

As described above, the blocks are divided hierarchically (S761, S762). When the number of imaging parts coming into each of the blocks is below the threshold value, the block division is stopped. After the final block division is stopped, the imaging order of the imaging parts is decided in each of the blocks (S763, S765). Also in the decision, as the order of the blocks are decided in FIGS. 9(b) and (c), a shortest path is examined in the round-robin manner. FIG. 9(d) shows an example of the result. The arrows indicate imaging order decided for five image acquisition parts in the block. Further, when the number of the image acquisition regions in the block is not higher than the threshold value (S763), the order of the image acquisition regions in the block is decided (S765). On the other hand, when the number of the image acquisition regions in the block is higher than the threshold value, returning and calling of this process are performed (S764). And above processes are repeated until processing of all 9 blocks is completed (S766).

The defect orders in each of the blocks divided hierarchically are joined finally to decide a final defect order (S767). In the method shown here, the wafer region is hierarchically divided into blocks to find a shortest path of the image acquisition region in each of the blocks. It cannot be always a shortest path when the entire wafer is viewed. However, it is a sufficiently employable result as the quasi-optimal solution of the shortest path.

As described above, when the order of the imaged parts is decided, first, second and third stage moving velocities are decided as the second step of scheduling (S77).

Calculation of the second stage moving velocity (the stage moving velocity during imaging) will be described first. This velocity is decided from the positional relation between a beam-scanning region, that is, the area of the visual field and an imaging part as image. The area of the visual field is a value decided from a characteristic such as beam distortion of the imaging system, which is typically a rectangular region being several hundred micrometers to several millimeters square.

Figure 10A:
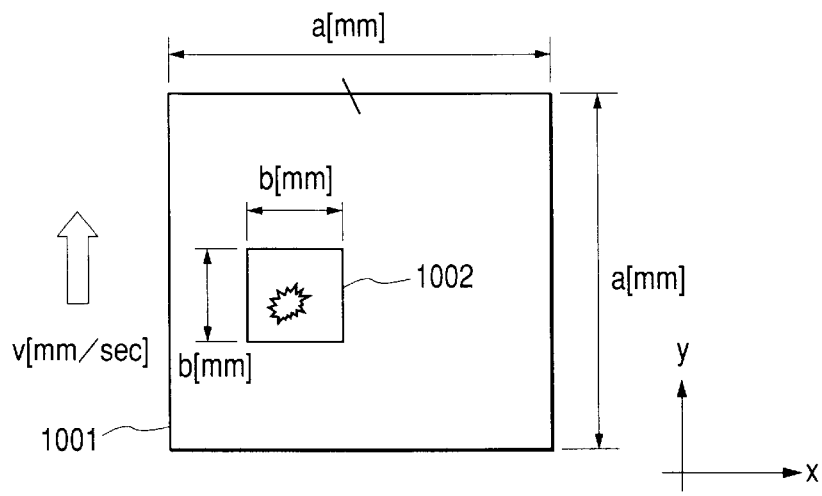
FIG. 10 is a diagram of assistance in explaining a calculation equation of a stage moving velocity according to the present invention.

FIG. 10 shows a schematic diagram of an observed part when viewed from top. A rectangular region 1001 shows a beam-scanning region. An optional rectangular region included within the range, e.g., an imaging rectangular region 1002 is scanned by the electron beam in two dimensions of the x and y directions. A two-dimensional image of the region 1002 part can be acquired. Here, it is shown that a suitable stage moving velocity is given corresponding to the image region imaging by the present invention to efficiently acquire an image.

When the stage continues to move without stopping, the scan region 1001 in FIG. 10 is moved with time on the sample in the direction opposite to the stage moving direction. When by way of example, the stage is moved in the minus y direction in the drawing, the scan region 1001 is moved in the y direction shown in the drawing. The moving velocity is v[mm/sec], one side of the scan region when assumed to be a square is a[mm], and one side of the image region of the part to be imaged when assumed to be a square is b[mm]. Naturally, a>=b is necessary. Further, in the imaging region, the time required to scan the electron beam in the x and y directions to acquire one image is s [sec/pieces]. The number of the frame addition is f[pieces].

Figure 10B:
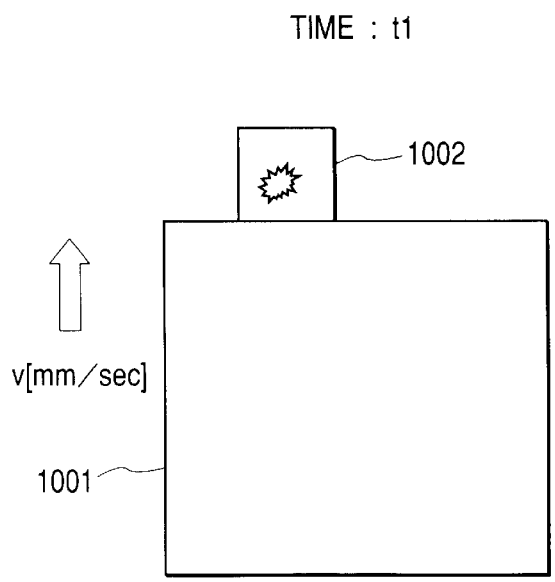
Figure 10C:
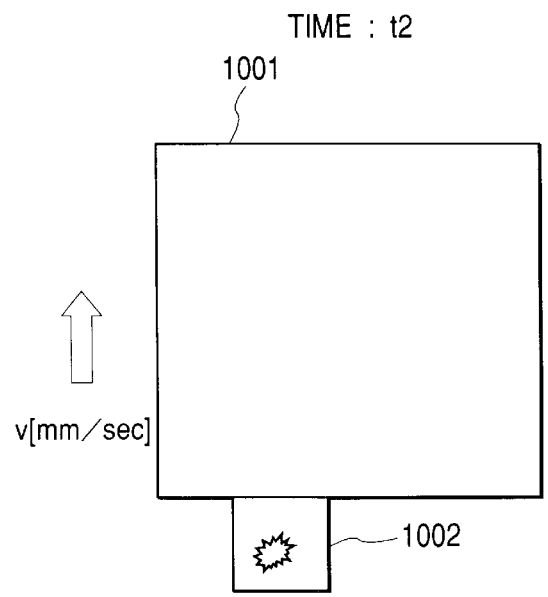

In FIG. 10, the electron beam is repeatedly scanned onto the imaging region 1002 in two dimensions of the x and y directions by f[pieces], the time required to acquire an image is s×f[sec]. Now, consider that the region 1001 includes only one imaging region 1002. Imaging must be performed from the time t1 of the positional relation between the region 1001 and the imaging region 1002, as shown in FIG. 10(b) to the time t2 of the positional relation between them, as shown in FIG. 10(c). The reason is that other than the period from t1 to t2, the electron beam cannot physically scan the region 1002. When the stage movement between t1 and t2 is performed with constant velocity v[mm/sec], the moving time between the period is (a−b)×v.

Since an image must be acquired during the moving time, the stage must be moved at a velocity v[mm/sec] to meet:

$$S \times f < (a-b)/v \qquad \text{Equation 1}$$

that is:

$$v < (a-b)/(s \times f) \qquad \text{Equation 2}$$

If the stage is driven at a velocity higher than the velocity v, before the completion of acquisition of the image of the region 1002, the region 1002 will stick out of the region 1001, whereby imaging cannot be performed correctly. On the other hand, when the stage is driven at a velocity lower than the v, an image can be acquired correctly, but the wasteful time is caused.

Figure 11A:
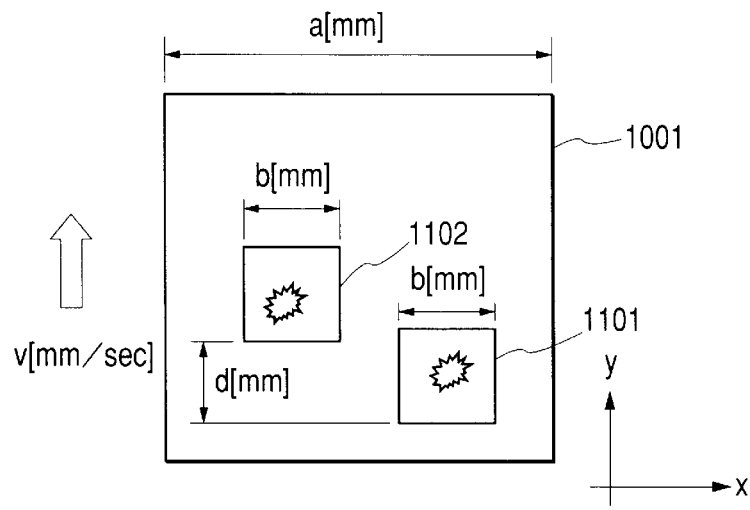
FIG. 11 is a diagram of assistance in explaining a calculation equation of a stage moving velocity according to the present invention.
Figure 11B:
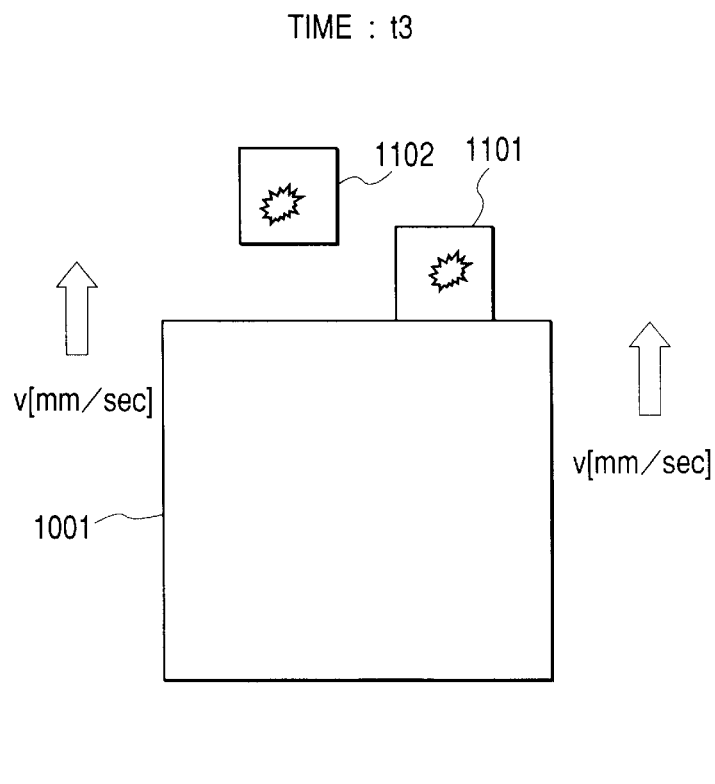
Figure 11C:
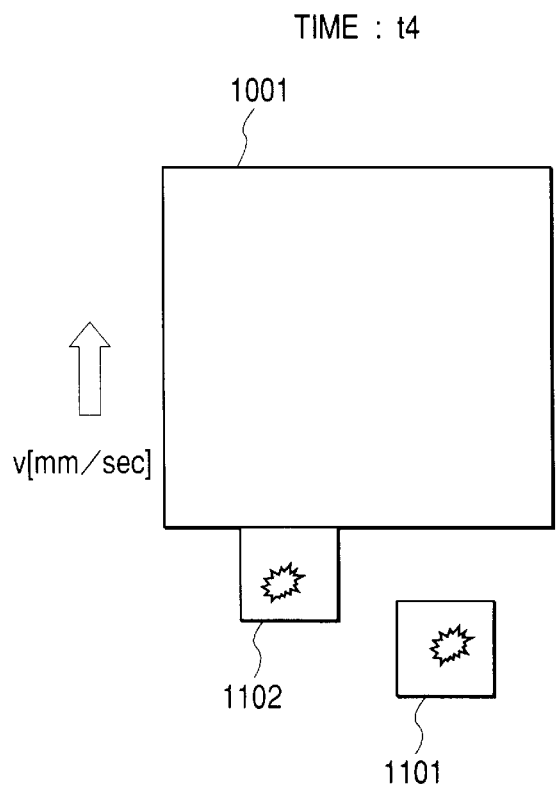

The case that a plurality of image acquisition regions exists in the scanning possible region will be described. By way of example, the case that two image acquisition regions exist will be described here. As shown in FIG. 11, two image acquisition regions 1101 and 1102 exist in the scan region 1001. In the regions 1101 and 1102, the relative distance in they direction is c[mm]. The two image acquisition regions are assumed to exist in the scanning possible region, which can be c<a. In this case, the two parts are imaged in the time interval from the time t3 shown in FIG. 11(b) to the time t4 shown in FIG. 11(c), at each of the times when the beam scan region and the imaged part are located. This time interval can be expressed as (a−b−c)×v.

In the case of that the region 1102 is scanned after the image acquisition region 1101 is scanned, as each of the scanning times is s×f[sec], it needs 2×s×f[sec] totally. The time to shift the electron beam to the scanning starting point of the region 1102 after the completion of scanning of the region 1101 is assumed to be much shorter than the actual scanning time, which is ignored. From the relation between the time required to acquire the image of the regions 1101 and 1102 and the stage moving velocity, v must meet:

$$S \times f < (a-b-c)/v \qquad \text{Equation 3}$$

that is, $$v < (a-b-c)/(2 \times s \times f) \qquad \text{Equation 4}$$

Figure 12:
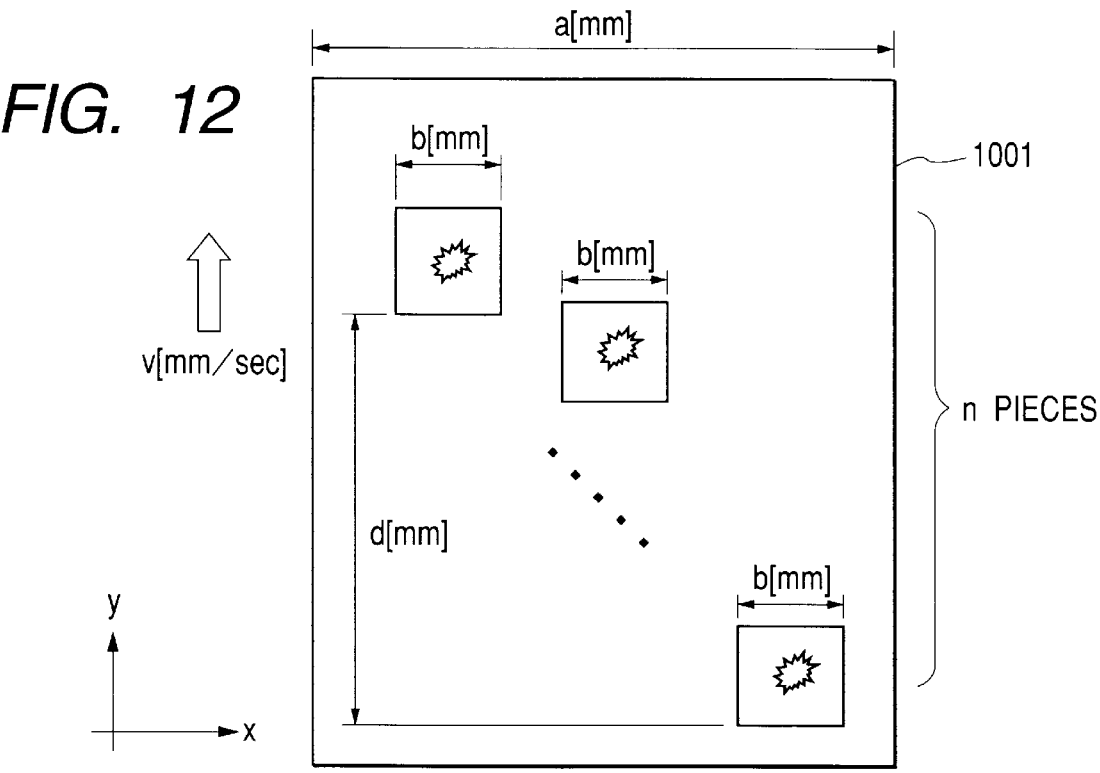
FIG. 12 is a diagram of assistance in explaining a calculation equation of a stage moving velocity according to the present invention.

In the similar idea, when n pieces of regions exist in one scan region, and the distance from the first region to the last region of n pieces of the regions in the stage moving direction is d[mm], as shown in FIG. 12, v must meet:

$$v < (a-b-c)/(n \times s \times f) \qquad \text{Equation 5}$$

This means that since the image acquisition parts are crowded together qualitatively, the more defects are included in the scan region, the lower the stage driving velocity in the part must be.

In the present invention, the stage is moved fast between the imaging parts as image. Then, while the imaging part is included within the beam scanning range, the stage can be driven at an upper limit velocity v[mm/sec] to meet the equation 5. As a result, imaging can be performed efficiently.

Figure 13:
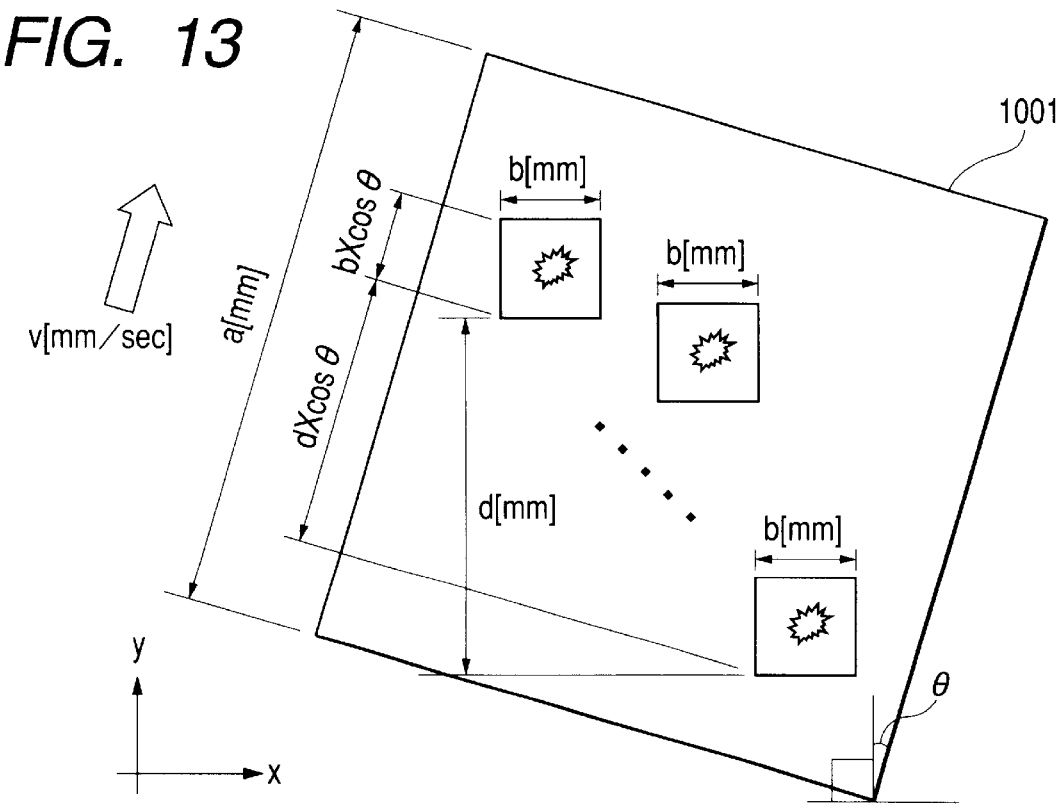
FIG. 13 is a diagram of assistance in explaining a calculation equation of a stage moving velocity according to the present invention.

The above-mentioned description shows the case that the stage is moved in the y direction and the image is scanned in the x and y directions, that is, the case that any one of the image scanning directions is the same as the stage moving direction. As shown in FIG. 13, when neither the stage moving direction nor the scanning direction correspond with each other, the present invention can be applied. FIG. 13 shows the case that the stage moving direction is different from the scanning direction by θ. In this case, an optimal stage driving velocity can be given by applying that b and d of the equation 5 are replaced with b×cos θ and d×cos θ.

A first and third stage moving velocities (the stage velocities when the stage is moved between the imaging parts) are decided. In order to collect images fast, the velocities may be set to a highest velocity capable of stably driving the stage of the apparatus. As a result, the stage can be moved between the imaged parts for a shortest time. In order to simplify control acceleration or deceleration from the stage moving velocity during imaging, these velocities may be also set to the same as the second stage moving velocity.

Further, a certain threshold value is provided. Then, when the distance between two imaged parts is larger than the threshold value, it is to set to a highest velocity capable of stably driving the stage and when it is smaller than the threshold value, it is possible to set to the same as the second velocity.

As describe above, the order of the parts to be imaged, the stage moving velocity during imaging (the second stage moving velocity), and the stage moving velocities between the imaging parts (the first and third stage moving velocities) are inspected by performing scheduling consisting of two steps. As a result, the time required to review the given imaged parts can be estimated previously.

Figure 14A:
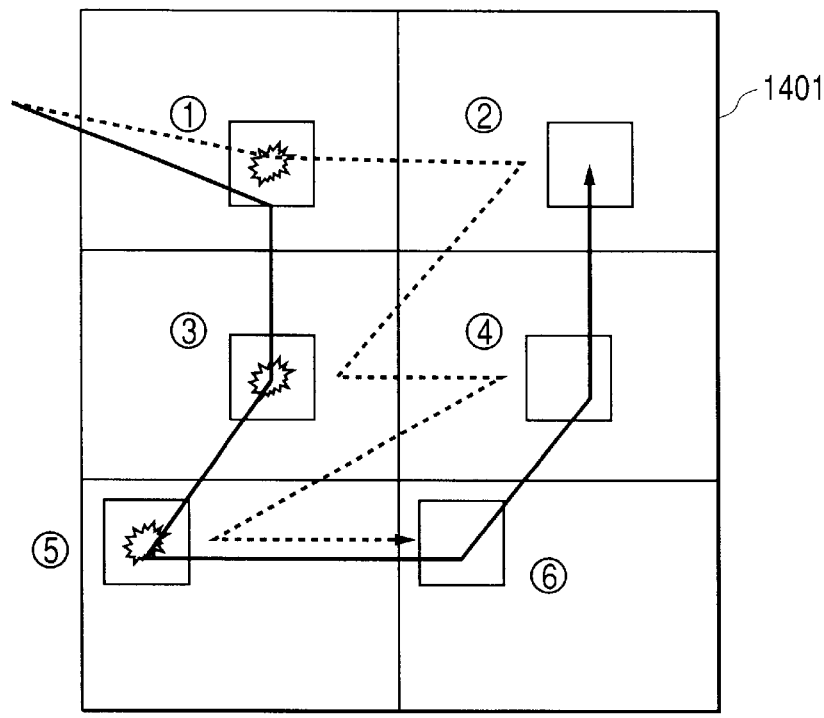
FIG. 14 is a diagram showing an effect of the imaging scheduling according to the present invention.

FIG. 14 is of assistance in explaining one example of the image acquisition sequence when the imaging scheduling of the present invention is performed. FIG. 14(a) shows six semiconductor chips 1401. Consider that parts ① to ⑥ in FIG. 14(a) are acquired as an image. ①③⑤ are parts detected by the defect inspection unit, and ②④⑥ are reference parts thereof. In the prior art, imaging is performed in the order indicated by the dot line in the drawing. In the present invention, imaging is performed in the order indicated by the solid line in the drawing. This is a result in which the imaging order is decided so that the stage moving distance is shortest.

Figure 14B:
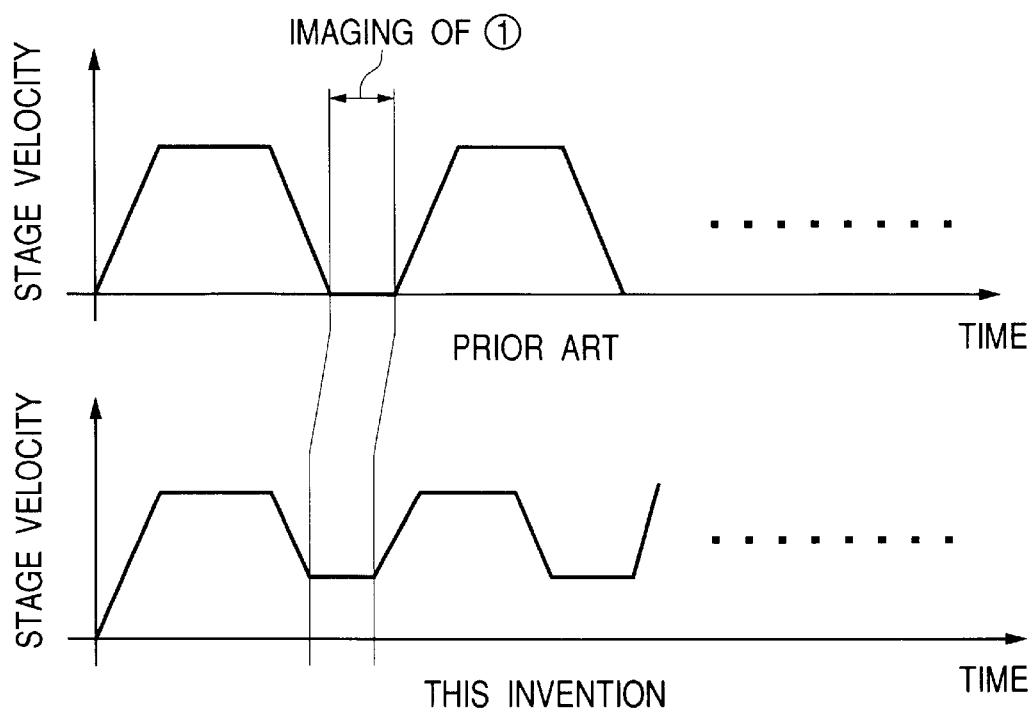

FIG. 14(b) shows the velocity change of the stage movement for acquisition of the image. The imaging sequence of the present invention shows a state that imaging is performed without stopping the stage. The imaging starting timing of the region ① is faster than that of the prior art. The reason is that in the present invention, the time to stop the stage must not be waited, unlike the prior art. In this manner, an image can be acquired faster than the prior art in which the stage is stopped for each of the imaging parts to perform imaging.

The throughput of the review unit of the present invention will be examined here. First, consider a beam electric current and the number of frames. In the throughput test-calculation of the prior art, the beam electric current is 200 pA with 16 frames. In the present invention, an electron gun capable of irradiating a beam of high electric current is used to provide the beam electric current amount of 800 pA which is four times larger than that of the prior art. As a result, the totalizing number of the frame is 4 to provide the same image quality as in the prior art. The image detection speed is 100 MHz (10 [nsec/pixels]) as in the throughput test-calculation of the prior art. The visual field of the imaging system is 500 [μm]×500 [μm]. To realize such a large visual field, the above-mentioned deflection correction must be essential.

The size of a defect is typically several μm. The imaging region is 5 [μm]×5 [μm] here. This region is captured into a digital image of 512×512. In this case, the time required to acquire an image of this region is 512×512×10 [nsec]=3 [msec]. When the stage moving velocity is v[mm/sec], the imaging time of one frame is 3 [msec], and the number of the frame is 4. The equation to be met by v is determined by the equation 2 as follows.

$$v < (a-b)/(s \times f)$$
$$= ((500-5) \times 10^{-3})/(3 \times 10^{-3} \times 4)$$
$$= 41.25 [\text{mm/sec}]$$

In the test-calculation below, the stage moving velocity during imaging is 40 [mm/sec].

As in the test-calculation in the prior art, defects are scattered uniformly on a wafer. The interval between the defect parts is 15 mm, and the interval between the defect part and the reference part to the defect is also 15 mm. The stage movement between the defect parts, or the stage movement between the defect part and the reference part is performed at a maximum velocity capable of stably moving the stage. The value is 100 [mm/sec] here. Imaging needs control of auto focus. The present invention uses a sensor, not shown, for detecting the wafer height direction of the imaged part to the stage movement in real time. The time to control auto focus is unnecessary.

In this case, the imaging order of the present invention consists of four steps for: (1) moving to the defect part at the first stage moving velocity (stage movement by 15 mm), (2) imaging while moving the stage at the second stage moving velocity, (3) moving to the reference part at the third stage moving velocity (stage movement by 15 mm), and (4) imaging while moving the stage at the second stage moving velocity. As in the throughput test-calculation of the prior art, the time to accelerate or decelerate the stage is ignored. The time required to image one defect is approximately:

$$15/100[\text{sec}] + 12[\text{msec}] + 15/100[\text{sec}] + 12[\text{msec}]$$
$$= 150[\text{msec}] + 12[\text{msec}] + 150[\text{msec}] + 12[\text{msec}]$$
$$= 324[\text{msec}]$$

In this case, the throughput is 11111 DPH, which can review 10000 defects per hour. In the above test-calculation, it is considered the case that the defects are scattered uniformly, that is, the case that only one defect exists in the imaging visual field of 500 [$\mu$m]×500 [$\mu$m]. When the number of defects is high and a plurality of defects are included in one visual field, a plurality of images can be imaged at the same time with once an imaging timing. The throughput is thus faster. It is expected that the throughput of the present invention can be about five times or more high than that of the prior art.

Figure 15:
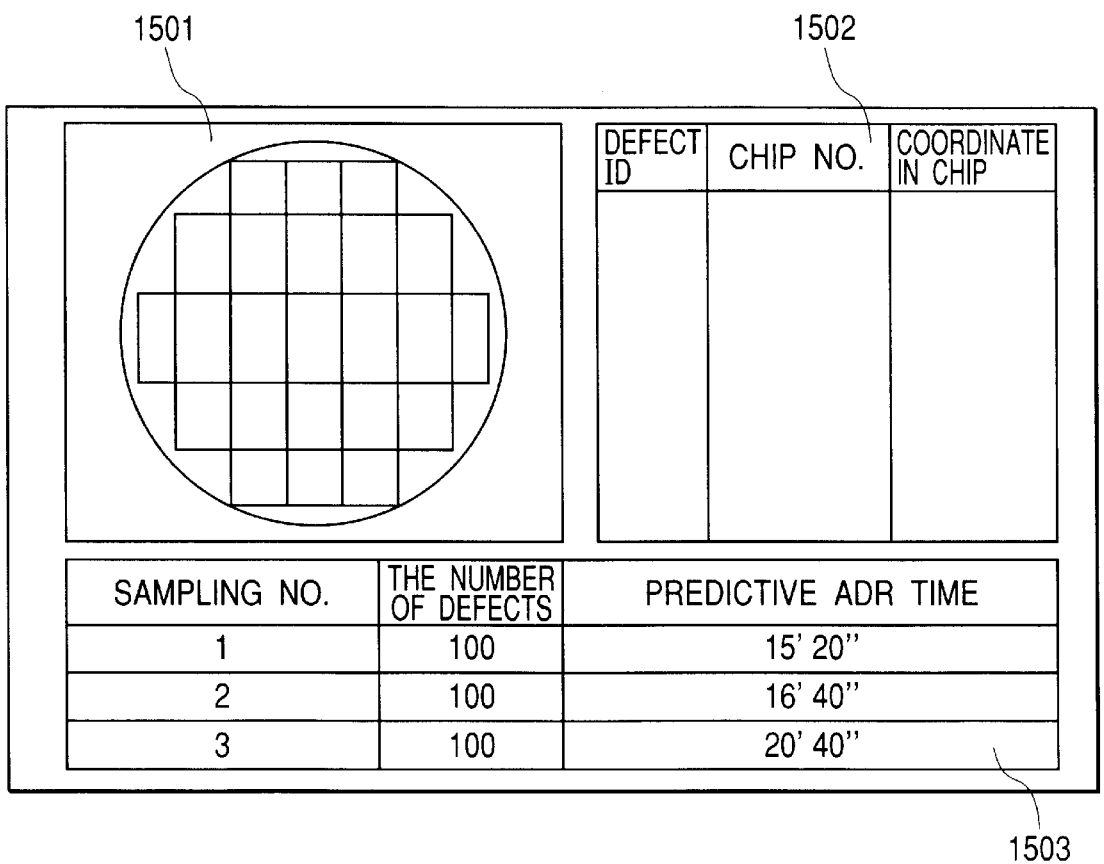
FIG. 15 is a diagram showing one example of a screen displaying an instruction of the imaging scheduling and the scheduling result according to the present invention.

FIG. 15 shows one example of a screen displayed on the input/output portion 501 in the image collection apparatus of the present invention. On a wafer map 1501, the position of the defect existing on the wafer is displayed together with a chip arrangement pattern formed on the wafer. A defect list 1502 displays a listing of the defects. The display contents are a defect ID of each of the defects, a chip position (X and Y), and a coordinate in the chips.

When the total number of the defects displayed on the wafer map is sufficiently high or the time for review is limited, all the defects are not subject to ADR, but only a plurality of defects selected (sampled) from all the defects may be subject to ADR. The number of the defects to be sampled may be specified by the operator, or the fixed value may be held in the apparatus. A percentage value x, that is, x[%] of the number of all the defects may be set by the user, or may be held as the inherent value in the apparatus.

Figure 16:
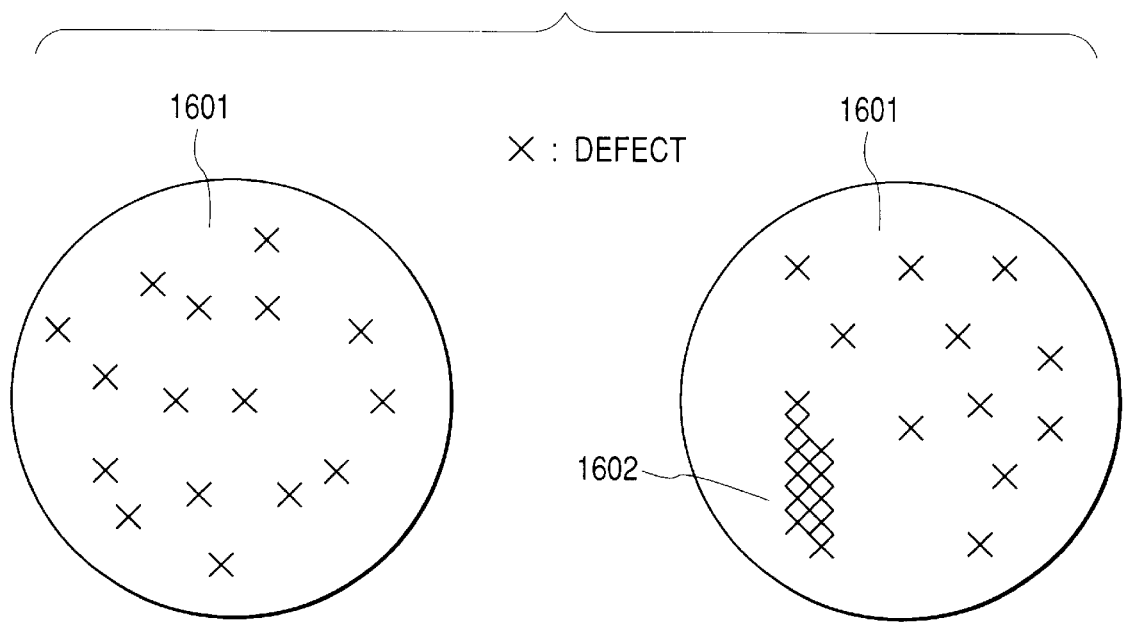
FIG. 16 is a diagram of assistance in explaining defect sampling according to the present invention.

In the case of FIG. 16(a) in which each position of defects are distributed at random on a wafer 1601, typically, the defect is selected at random from these to be subject to ADR. Further, in the case that defects 1602 are dense locally as shown in FIG. 16(b), defects are often caused by the same cause in the part in which these are dense. Many of the defects 1602 need not be subject to ADR.

In such a case, in the apparatus, the defects are classified into a part in which such defects are dense and a random part other than that. Then, the defects are sampled automatically for each of the parts. In one of the above-mentioned classification methods in the apparatus, a shortest distance between each of the defects and other defect is determined so as to classify the dense defects having such a shortest distance smaller than a certain threshold value and other defects not having the same.

The user previously sets a population to be sampled. The apparatus samples one or more defects from the population. The scheduling result of each of the samplings can be displayed on a scheduling result display part 1503. In the population, only defects existing in one or more specific chips on the wafer is a population of sampling, only defects in which the defect number is included in a certain range is a population of sampling, and the number of defects sampled from such a population is specified.

Without automatic sampling as described above, the given number of defects are manually selected from the wafer map 1501 or the defect list 1502. Then, scheduling for ADR optimal for the selected defect can be performed to present the result to the user. The user can add or delete the defect to be subject to ADR by using the wafer map 1501 or the defect list 1502 to select the defect under the presenting result. The scheduling result is displayed on the display part 1503.

The automatic sampling and the manual sampling are combined with each other; that is, the user can add or delete the given defect to the automatic sampling result.

In the image collection apparatus according to the present invention, the above-mentioned automatic or manual defect sampling is performed several times. ADR scheduling is performed to the sampling results. ADR time predicted in each of the samplings is calculated, which is then displayed the scheduling result display part 1503. The ADR prediction time can be calculated from the number of the defects, the moving distance between the defects, and the time to image the defect.

The display part 1503 in FIG. 15 shows the case that by way of example, the sampling defect number is 100, and three samplings are performed in the apparatus to display prediction ADR times to each of the samplings in the shortest order. When each of the samplings on the display part 1503 is specified by some method such as mouse click on the screen, only the defect selected as the sampling result is highlighted on the wafer map 1501 or the defect list 1502. As a result, the relation between the selected defect positional relation and the prediction ADR time can be expressed clearly. The user can select the sampling to be actually subject to ADR from the plurality of samplings displayed on the screen.

Selection of the sampling to be actually subject to ADR from the plurality of samplings can be performed not only manually by the operator, as described above, but also automatically in the apparatus so that the shortest prediction ADR time is selected.

In this manner, one or more samplings are performed in accordance with the population or the sampling defect number optionally specified by the user, from which the user selects the sampling to be actually subject to ADR, thereby performing various samplings.

In the above-mentioned image collection apparatus and method according to the present invention, the defect images of a large number of defects existing on a semiconductor wafer can be collected efficiently. Further, the cause of the defects is analyzed efficiently so as to reduce a period to solve the defect cause. The present invention can be applied not only to reviewing of defects caused on the semiconductor wafer but also to reviewing of defects of any industrial product. The present invention can be also applied not only to the case that the review target is a defect, but also to the case that it is a given observed part set by the user.

According to the present invention, the image of a defect part caused in the semiconductor wafer production process can be collected efficiently, which can be classified automatically. When the number of defects existing in one wafer is very high, the defect images thereof can be colleted for a short time and the time to specifying the defect cause can be reduced.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An image classification method comprising the steps of:

irradiating sequentially an electron beam of a scanning electron microscope onto a plurality of parts to be observed on a sample by controlling the electron beam based on positional information of a stage and positional information of said plurality of parts while moving the stage with the sample placed thereon;

acquiring a secondary electronic image of each of said plurality of parts to be observed on the sample by detecting a secondary electron radiated from the sample when the electron beam is irradiated onto said sample while moving the stage;

classifying each of the acquired secondary electronic images; and wherein the stage is moved between said plurality of parts to be observed on the sample at a velocity higher than that when the secondary electronic image of said part to be observed on the sample is acquired while moving the stage.

2. The image classification method according to claim 1, wherein order to image said plurality of parts to be imaged on the sample, stage moving velocity to sequentially place the plurality of parts into an imaging visual field, and stage velocity when imaging said each of the parts are decided previously before imaging, thereby controlling movement of said stage based on contents decided.

3. The image classification method according to claim 1, wherein said step of classifying includes step of classifying said acquired secondary electronic image based on feature amount of said secondary electronic image.

4. The image classification method according to claim 3, wherein said feature amount of the secondary electronic image includes any one of brightness feature amount and shape feature amount of the electronic secondary image.

5. The image classification method according to claim 1, wherein said step of acquiring includes step of acquiring secondary electronic images of 10000 or more parts to be observed for one hour by being performed to acquire sequentially the secondary electronic image for the plurality of the parts to be observed while moving the stage in a state that said parts to be observed are placed into an observation visual field.

6. An apparatus for observing a sample comprising:

a stage unit which has a stage placed the sample thereon for movement;

a position detector which detects position of the stage;

a scanning electron microscope unit which acquires an electron beam image of surface of said sample by irradiating and scanning an electron beam focused onto the sample placed on said stage;

a control unit which controls the movement of said stage and a range to be scanned by irradiating the electron beam of said scanning electron microscope unit based on positional information of said stage detected by said position detector and positional information of a plurality of locations to be observed on said sample;

an image classification unit which classifies the electron beam image of the surface of said sample acquired by said scanning electron microscope unit; and wherein the control unit controls said stage unit so that moving velocity of said stage when the plurality of locations to be observed on said sample are moved so as to sequentially be placed into imaging visual field of said scanning electron microscope unit is higher than moving velocity of said stage when location to be observed on said sample is moved in the imaging visual field of said scanning electron microscope unit.

7. The apparatus for observing a sample according to claim 6, wherein said image classification unit classifies said acquired electron beam image based on feature amount of the electron beam image.

8. The apparatus for observing a sample according to claim 7, wherein the feature amount of the electron beam image includes any one of brightness feature amount and shape feature amount of the electron beam image.

* * * * *